United States Patent
Limburg et al.

(10) Patent No.: US 11,781,973 B2
(45) Date of Patent: Oct. 10, 2023

(54) METHODS AND SYSTEMS FOR CALIBRATING AND USING A CAMERA FOR DETECTING AN ANALYTE IN A SAMPLE

(71) Applicant: Roche Diabetes Care, Inc., Indianapolis, IN (US)

(72) Inventors: Bernd Limburg, Soergenloch (DE); Max Berg, Mannheim (DE); Fredrik Hailer, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 680 days.

(21) Appl. No.: 17/001,363

(22) Filed: Aug. 24, 2020

(65) Prior Publication Data

US 2020/0386672 A1 Dec. 10, 2020

Related U.S. Application Data

(63) Continuation of application No. PCT/EP2019/054583, filed on Feb. 25, 2019.

(30) Foreign Application Priority Data

Feb. 26, 2018 (EP) .................................... 18158626

(51) Int. Cl.
*G01N 21/27* (2006.01)
*G01N 21/78* (2006.01)
(Continued)

(52) U.S. Cl.
CPC ......... *G01N 21/274* (2013.01); *G01N 21/272* (2013.01); *G01N 21/78* (2013.01);
(Continued)

(58) Field of Classification Search
None
See application file for complete search history.

(56) References Cited

U.S. PATENT DOCUMENTS

| 9,442,089 B2 | 9/2016 | Massari et al. |
| 2008/0267446 A1 | 10/2008 | Capewell |

(Continued)

FOREIGN PATENT DOCUMENTS

| CN | 104122213 A | 10/2014 |
| CN | 104812292 A | 7/2015 |

(Continued)

OTHER PUBLICATIONS

Li et al., Water Quality Monitoring Method of Point Source Based on Colorimetric of Remote Image, Chinese Journal of Environmental Engineering, Sep. 5, 2015, vol. 9, No. pp. 4603-4608.

(Continued)

*Primary Examiner* — Hoon K Song
(74) *Attorney, Agent, or Firm* — Bose McKinney & Evans LLP

(57) ABSTRACT

A calibration method for calibrating a camera for detecting an analyte in a sample is disclosed. A plurality of different color coordinate systems and a set of test samples are provided. The test samples are applied to test elements that have test fields for producing an optically detectable reaction. Images of the colored test fields are acquired using the camera and color coordinates for the images are generated. The color coordinates that are generated are transformed into a set of measured concentrations by using a set of coding functions. The set of measured concentrations is compared with the known concentrations of the test samples and a best match color coordinate system of the plurality of color coordinate systems is determined. A best match coding function of the plurality of coding functions is also determined.

13 Claims, 9 Drawing Sheets

(51) Int. Cl.
*G01N 21/84* (2006.01)
*G01N 33/68* (2006.01)
*G06F 17/18* (2006.01)

(52) U.S. Cl.
CPC ..... *G01N 21/8483* (2013.01); *G01N 33/6893* (2013.01); *G06F 17/18* (2013.01)

(56) References Cited

U.S. PATENT DOCUMENTS

| | | | |
|---|---|---|---|
| 2014/0072189 | A1 | 3/2014 | Jena et al. |
| 2015/0055134 | A1 | 2/2015 | Papautsky et al. |
| 2015/0241358 | A1* | 8/2015 | Burg ................... G01N 21/272 422/402 |
| 2015/0359458 | A1 | 12/2015 | Erickson et al. |
| 2016/0004900 | A1* | 1/2016 | Revie ................... G01N 33/487 382/133 |
| 2016/0080548 | A1 | 3/2016 | Erickson et al. |
| 2016/0091433 | A1 | 3/2016 | Baxi et al. |
| 2017/0067832 | A1 | 3/2017 | Ferrara, Jr. et al. |
| 2017/0074783 | A1 | 3/2017 | Dadlani Dadlani et al. |
| 2017/0184506 | A1 | 6/2017 | Patel |
| 2019/0137340 | A1* | 5/2019 | Ogino ................... G01N 21/274 |

FOREIGN PATENT DOCUMENTS

| | | |
|---|---|---|
| CN | 105164514 A | 12/2015 |
| CN | 105675507 A | 6/2016 |
| CN | 106068449 A | 11/2016 |
| CN | 107240089 A | 10/2017 |
| EP | 1 963 828 B1 | 3/2010 |
| EP | 2 916 117 A1 | 9/2015 |
| JP | H 10-73534 A | 3/1998 |
| JP | 2003-262591 A | 9/2003 |
| JP | 2007-101482 A | 4/2007 |
| JP | 2011-191081 A | 9/2011 |
| JP | 2015-509582 A | 3/2015 |
| JP | 2015-536465 A | 12/2015 |
| KR | 10-2015-0123962 A | 11/2015 |
| TW | 201441619 A | 11/2014 |
| WO | WO 2007/120279 A2 | 10/2007 |
| WO | WO 2014/037820 A2 | 3/2014 |
| WO | WO 2015/164991 A2 | 11/2015 |
| WO | WO 2016/025935 A2 | 2/2016 |

OTHER PUBLICATIONS

Chai et al., Detecting Chlorophyll Content of Tomato Leaves with Technology of Computer Vision, Acta Horticulture Sincica, Dec. 31, 2009, vol. 36, No. 1, pp. 45-52.
International Search Report and Written Opinion of the International Searching Authority, PCT/EP2019/054583, dated May 16, 2019, 15 pages.
Hönes et al., Diabetes Technology and Therapeutics, vol. 10, Supplement 1, 2008, pp. 10-26.
Shen et al., Point-of-Care Colorimetric Detection with a Smartphone, Lab on a Chip, Jan. 1, 2012, vol. 12, No. 21, 4 pages.
Thomas et al., The Colorimetric Determination of Selectively Cleaved Adenosines and Guanosines in DNA Oligomers Using Bicinchoninic Acid and Copper, Journal of Biological Inorganic Chemistry, Nov. 2, 2016, vol. 22, No. 1, pp. 31-46.
Yetisen et al., A Smartphone Algorithm with Inter-Phone Repeatability for the Analysis of Colorimetric Tests, Sensors and Actuators B: Chemical, International Journal Devoted to Research and Development of Physical and Chemical Transducers, Feb. 12, 2014, vol. 196, pp. 156-160.
Ming-Yan et al., The Calibration of Cellphone Camera-Based Colorimetric Sensor Array and Its Application in the Determination of Glucose in Urine, Biosensors and Bioelectronics, Dec. 1, 2015, vol. 74, pp. 1029-1037.
Clarke et al., Evaluating Clinical Accuracy of Systems for Self-Monitoring of Blood Glucose, Diabetes Care, Sep.-Oct. 1987, vol. 10, No. 5, pp. 622-628.
König, F., Die Charakterisierung von Farbsensoren (The Characterization of Color Sensors), Dissertation, Logos Verlag, Berlin, 2001, pp. 48-49.

* cited by examiner

METHODS AND SYSTEMS FOR CALIBRATING AND USING A CAMERA FOR DETECTING AN ANALYTE IN A SAMPLE

RELATED APPLICATIONS

This application is a continuation of PCT/EP2019/054583, filed Feb. 25, 2019, which claims priority to EP 18 158 626.4, filed Feb. 26, 2018, the entire disclosures of both of which are hereby incorporated herein by reference.

BACKGROUND

The present application refers to a calibration method for calibrating a camera for detecting an analyte in a sample. This disclosure further relates to a detection method for detecting an analyte in a sample and a computer program for executing the calibration method or the detection method. Further, this disclosure relates to a calibration system for calibrating a camera for the purpose of detecting an analyte in a sample by using the camera, a detection system for detecting an analyte in a sample by using at least one test element, and a system for detecting an analyte in a sample. Methods, computer programs and systems according to this disclosure may be used in medical diagnostics, in order to qualitatively or quantitatively detect one or more analytes in one or more body fluids. Other fields of application of this disclosure are possible.

Medical diagnostics, in many cases, requires one or more analytes to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. In general, devices and methods known to the skilled person for detecting analytes make use of test elements comprising one or more test chemistries, which, in presence of the analyte to be detected, are capable of performing one or more detectable detection reactions, such as optically detectable detection reactions. With regard to these test chemistries, reference may be made, e.g., to J. Hoenes et al.: The Technology Behind Glucose Meters: Test Strips, Diabetes Technology & Therapeutics, Volume 10, Supplement 1, 2008, S-10 to S-26. According to the concentration and/or the presence of the analyte, an appropriate treatment may be chosen, if necessary.

Typically, one or more optically detectable changes in the test chemistry are monitored, in order to derive the concentration of the at least one analyte to be detected from these changes. For detecting the at least one change of optical properties of the test field, various types of detectors are known in the art. Thus, various types of light sources for illuminating the test fields as well as various types of detectors are known. Besides using customized detectors which are specifically developed for the purpose of optically detecting changes in the test chemistry comprised by corresponding test elements, recent developments aim at using widely available devices such as smartphones.

As an example, Li Shen et al.: "Point-of-care colorimetric detection with a smartphone," Lab Chip, 2012, 12, 4240-4243, "The Royal Society of Chemistry," and corresponding Electronic Supplementary Material (ESI) for Lab on a Chip, "The Royal Society of Chemistry" propose performing a colorimetric detection with a smart phone. Colors of colorimetric diagnostic assays or quantified with a smart phone that allows high accuracy measurements in a wide range of ambient conditions. Instead of directly using the red, green, and blue (RGB) intensities of a color image taken by the smartphone, chromaticity values are used to construct calibration curves of analyte concentrations. Further, to make the approach adoptable under different lighting conditions, a calibration technique to compensate for measurement errors due to variability in ambient light was developed.

Generally, when using smart phones or other consumer-electronics having a camera for the purpose of evaluating analytical measurements, individual calibration of the camera is necessary. Thus, Ali K. Yetisen et al.: "A smartphone algorithm with inter-phone repeatability for the analysis of colorimetric tests," Sensors and Actuators B 196 (2014) 156-160, proposes a smartphone algorithm with inter-phone repeatability for the analysis of colorimetric tests, requiring a user to perform a calibration entry by entering information into the smartphone and capturing an image of various calibration points using the camera of the smartphone. The calibration needs to be performed under predefined conditions. Subsequently the colorimetric measurements may be performed using exactly the same conditions as for the performing of the calibration. The app computes the final measurement by comparing the target data values with respect to the calibration curve. This is achieved by an interpolation algorithm similar to the nearest neighbor problem in computational geometry.

Another calibration approach is proposed in WO 2014/037820 A2, disclosing a system and method for analysis of colorimetric test strips and disease management. The system can include an accessory that is operably coupled to a mobile device, the mobile acquiring and/or analyzing images of the colorimetric test strips. The light box accessory can be detachably attached to the mobile device, or made to remain attached to the mobile device, but with the capability of having the light box accessory removed from the field of view of the camera for general photography purposes. In other embodiments, an image containing known calibration colors and reagent areas is obtained sans the lightbox for comparison with a previous calibration image to model changes in ambient lighting conditions and determine a color correction function. The correction can be applied to the detected reagent area colors for matching between the detected reagent area colors and reference colors on the reference chart.

Despite the advantages involved in calibrating and using a camera, e.g., a camera comprised by consumer-electronics, for the purpose of detecting an analyte in a sample, several technical challenges remain. In general, color representation in camera systems is adapted to provide images which are optimized in terms of human color perception, e.g., by internal post-processing of the raw data captured by the camera. However, such post-processing due to human color perception may not be ideal when aiming at accurately determining analyte concentrations in the sample. Additionally, non-linear factors, such as different lighting conditions or individual technical and optical properties of a huge number of cameras available on the market, may have an impact on the determination of the analyte concentration and therefore need to be taken into account.

SUMMARY

This disclosure teaches methods, computer programs and systems which address the above-mentioned technical challenges for calibrating a camera for detecting an analyte in a sample, for example for calibrating cameras comprised by mobile devices such as consumer-electronics mobile devices, specifically multipurpose mobile devices which are not dedicated to analytical measurements such as smart phones or tablet computers. Specifically, methods, computer programs and systems are disclosed which are widely applicable to available cameras and which are suited to increase measurement accuracy and convenience for the user.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "test field," "test chemical," "color coordinate system," and "test element," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of this disclosure, a calibration method is disclosed, for calibrating a camera for the purpose of detecting an analyte in a sample. The method comprises the following steps which specifically may be performed in the given order. Still, a different order is also possible. It is further possible to perform two or more of the method steps fully or partially simultaneously. It is further possible to perform one or more method steps or even all of the method steps once or repeatedly. The method may comprise additional method steps which are not listed herein. Generally, the calibration method comprises the following steps:

a. providing a set of color coordinate systems, the set of color coordinate systems comprising a plurality of different color coordinate systems configured for describing a color of an object;

b. providing a set of test samples having known concentrations of the analyte;

c. applying the test samples to a set of test elements, each test element having at least one test field comprising at least one test chemical configured for performing an optically detectable detection reaction with the analyte, thereby creating at least one colored test field for each of the test samples;

d. acquiring images of the colored test fields by using the camera;

e. generating color coordinates for the images of the colored test fields, by using the color coordinate systems of the set of color coordinate systems, thereby creating a set of color coordinates for the test samples and for the color coordinate systems;

f. providing a set of coding functions, the set of coding functions comprising a plurality of coding functions for transforming color coordinates of a test field into a corresponding concentration of the analyte in the sample;

g. transforming the set of color coordinates generated in step e. into a set of measured concentrations by using the set of coding functions; and h. comparing the set of measured concentrations with the known concentrations of the test samples of the set of test samples and determining a best match color coordinate system of the set of color coordinate systems and a best match coding function of the set of coding functions for which the set of measured concentrations best matches with the known concentrations.

The term "calibration method for calibrating a camera for detecting an analyte in a sample" as used herein is a broad term and is to be given its ordinary and customary meaning to a person of ordinary skill in the art and is not to be limited to a special or customized meaning. The term specifically may refer, without limitation, to the process of determining a relationship between information provided by a camera and the presence or absence or the concentration of one or more specific analytes in the sample. Thus, typically, the camera will generate information, such as electronic information, such as one or more images, such as one or more images of at least one test field as will be explained in further detail below. Generally, there may exist a relationship between the information or a part thereof and the presence, absence or concentration of the analyte in the sample, such as when the camera takes one or more images of a test field wetted by the sample. The process of determining this relationship may be referred to as the calibration method. As a result of the calibration method, the relationship may be defined, such as by defining one or more of at least one equation defining the relationship, at least one table such as at least one lookup table for defining the relationship, or at least one graphic relationship such as at least one calibration curve.

The term "camera" as used herein is a broad term and is to be given its ordinary and customary meaning to a person of ordinary skill in the art and is not to be limited to a special or customized meaning. The term specifically may refer, without limitation, to a device configured for recording spatially resolved optical data, such as one or more images. The camera specifically may comprise one or more camera chips are imaging devices, such as one or more CCD and/or CMOS chips. The camera generally may comprise a one-dimensional or two-dimensional array of image sensors, such as pixels. As an example, the camera may comprise at least 10 pixels in at least one dimension, such as at least 10 pixels in each dimension. It shall be noted, however, that other cameras are also feasible. This disclosure specifically shall be applicable to cameras as usually used in mobile applications such as notebook computers, tablets or, specifically, cell phones such as smart phones. Thus, specifically, the camera may be part of a mobile device which, besides the at least one camera, comprises one or more data processing devices such as one or more data processors. Other cameras, however, are feasible. The camera, besides at least one camera chip or imaging chip, may comprise further elements, such as one or more optical elements, e.g., one or more lenses. As an example, the camera may be a fix-focus camera, having at least one lens which is fixedly adjusted with respect to the camera. Alternatively, however, the camera may also comprise one or more variable lenses which may be adjusted, automatically or manually.

The term "detecting an analyte in a sample," often also referred to as an "analytical measurement," as used herein is a broad term and is to be given its ordinary and customary meaning to a person of ordinary skill in the art and is not to be limited to a special or customized meaning. The term specifically may refer, without limitation, to a qualitative and/or quantitative determination of at least one analyte in the sample. The result of the analytical measurement, as an example, may be a concentration of the analyte and/or the presence or absence of the analyte to be determined.

The term "image" as used herein is a broad term and is to be given its ordinary and customary meaning to a person of ordinary skill in the art and is not to be limited to a special or customized meaning. The term specifically may refer, without limitation, to data or information recorded by using the camera, such as a plurality of electronic readings from the imaging device, such as the pixels of the camera chip. Thus, as an example, the image may comprise a one-dimensional or two-dimensional array of data. The image itself, thus, may comprise pixels, the pixels of the image, as an example, correlating to pixels of the camera chip. Consequently, when referring to "pixels," reference is either made to the units of image information generated by the single pixels of the camera chip or to the single pixels of the camera chip directly.

The camera specifically may be a color camera. Thus, such as for each pixel, color information may be provided or generated, such as color values for three colors R, G, B. a larger number of color values is also feasible, such as four colors for each pixel. Color cameras are generally known to the skilled person. Thus, as an example, each pixel of the camera chip may have three or more different color sensors, such as color recording pixels like one pixel for red (R), one pixel for yellow (G) and one pixel for blue (B). For each of the pixels, such as for R, G, B, values may be recorded by the pixels, such as digital values in the range of 0 to 255, depending on the intensity of the respective color. Instead of using color triples such as R, G, B, as an example, quadruples may be used, such as C, M, Y, K. The color sensitivities of the pixels may be generated by color filters or by appropriate intrinsic sensitivities of the sensor elements used in the camera pixels. These techniques are generally known to the skilled person.

The term "analyte" as used herein is a broad term and is to be given its ordinary and customary meaning to a person of ordinary skill in the art and is not to be limited to a special or customized meaning. The term specifically may refer, without limitation, to one or more specific chemical compounds and/or other parameters to be detected and/or measured. As an example, the at least one analyte may be a chemical compound which takes part in metabolism, such as one or more of glucose, cholesterol or triglycerides. Additionally or alternatively, other types of analytes or parameters may be determined, e.g., a pH value.

The term "sample" as used herein is a broad term and is to be given its ordinary and customary meaning to a person of ordinary skill in the art and is not to be limited to a special or customized meaning. The term specifically may refer, without limitation, to an amount of arbitrary material to be analyzed, such as one or more of a liquid, solid or gaseous material. More specifically, the term may refer to an amount of a bodily fluid, such as one or more of blood, interstitial fluid, urine, saliva or the like. Additionally or alternatively, however, other types of samples may be used, such as water.

The term "color coordinate system" as used herein is a broad term and is to be given its ordinary and customary meaning to a person of ordinary skill in the art and is not to be limited to a special or customized meaning. The term specifically may refer, without limitation, to an arbitrary coordinate system by which a color of an object, such as a color of a test field or a color of an image recorded by a camera, may be characterized, such as mathematically or physically. Various color coordinate systems are generally known to the skilled person, such as color coordinate systems defined by CIE. Various examples will be given below. The color coordinates, in their entirety, may span or define a color space, such as by defining three or four basis vectors.

For providing the color coordinate systems, these color coordinate systems may be stored, as an example, in a data storage device or database and/or may be defined by a general formula for the coordinate systems having one or more parameters. The color coordinate systems may be provided automatically or by human action. The color coordinate systems may be an input for the calibration method, provided by a user of the calibration method.

The term "test sample" as used herein is a broad term and is to be given its ordinary and customary meaning to a person of ordinary skill in the art and is not to be limited to a special or customized meaning. The term specifically may refer, without limitation, to a sample having a determined or determinable quantity or concentration of an analyte therein.

As further used herein, the term "set" generally refers to a defined quantity of identical or similar objects or elements with each object or element having known or determinable properties. Thus, generally, each set may contain two or more, more preferably three or more objects or elements. The set may contain a finite number of objects or elements or an infinite number of objects or elements.

Thus, as an example, the set of test samples generally may contain a plurality of at least two defined or determinable amounts of the sample. As an example, the set of test samples may contain a first quantity of the test sample having a first known or determinable concentration of the analyte, as well as at least one second quantity of the test sample having a second known or determinable concentration of the analyte therein, with the second concentration being different from the first concentration. Optionally, third, fourth and so forth quantities of the test sample may be contained in the set of test samples, having third, fourth and so forth concentrations of the analyte contained therein. Thus, as an example, the set of test samples may contain three or more different concentrations of the analyte in the test sample. As an example, the set of test samples may be provided in vials or other containers. The concentrations may be known by predetermining these concentrations, such as by using certified or reliable laboratory analysis and/or by preparing the test samples by using known amounts of the components. Alternatively, the concentrations may be known at a later point in time, such as by post-processing the test samples by subsequent analysis by using certified or reliable laboratory analysis methods.

The providing of the test samples may include the preparation of the test samples or other means of providing these test samples, such as purchase of these test samples from an appropriate provider. Other means of providing the test samples may be feasible.

The method may further comprise providing a set of test elements, each test element having at least one test field comprising at least one test chemical configured for performing an optically detectable detection reaction with the analyte.

The term "test element" as used herein is a broad term and is to be given its ordinary and customary meaning to a person of ordinary skill in the art and is not to be limited to a special or customized meaning. The term specifically may refer, without limitation, to an arbitrary element or device configured for detecting the analyte in the sample, specifically in the sense of the definition given above. The test element, as an example, may comprise at least one substrate, such as at least one carrier, with the at least one test field applied thereto or integrated therein. As an example, the at least one carrier may be strip-shaped, thereby rendering the test element a test strip. These test strips are generally widely in use and available. One test strip may carry a single test field or a plurality of test fields having identical or different test chemicals comprised therein. Several test elements are known in the art which comprise at least one test chemical, also referred to as a test reagent, which undergo a coloration reaction in the presence of the at least one analyte to be detected. Some basic principles on test elements and reagents that may also be used within the scope of this disclosure are described, e.g., in J. Hones et al.: Diabetes Technology and Therapeutics, Vol. 10, Supplement 1, 2008, pp. 10-26.

As further used herein, the term "test field" is a broad term and is to be given its ordinary and customary meaning to a person of ordinary skill in the art and is not to be limited to a special or customized meaning. The term specifically may refer, without limitation, to a coherent amount of the test chemical, such as to a field, e.g., a field of round, polygonal or rectangular shape, having one or more layers of material, with at least one layer of the test field having the test chemical comprised therein. Other layers may be present providing specific optical properties such as reflective properties, providing spreading properties for spreading the sample or providing separation properties such as for separating of particulate components of the sample, such as cellular components.

The term "test chemical" as used herein is a broad term and is to be given its ordinary and customary meaning to a person of ordinary skill in the art and is not to be limited to a special or customized meaning. The term specifically may refer, without limitation, to a chemical compound or a plurality of chemical compounds such as a mixture of chemical compounds suited for performing a detection reaction in the presence of the analyte, wherein the detection reaction is detectable by specific means, such as optically. The detection reaction specifically may be analyte-specific. The test chemical, in the present case, specifically may be an optical test chemical, such as a color-change test chemical which changes in color in the presence of the analyte. The color change specifically may depend on the amount of analyte present in the sample. The test chemical, as an example, may comprise at least one enzyme, such as glucose oxidase and/or glucose dehydrogenase. Additionally, other components may be present, such as one or more dyes, mediators and the like. Test chemicals are generally known to the skilled person and, again, reference may be made to J. Hones et al.: Diabetes Technology and Therapeutics, Vol. 10, Supplement 1, 2008, pp. 10-26. Other test chemicals, however, are feasible, too.

The set of test elements specifically may comprise a plurality of at least three test elements, such as at least three test elements of the same setup. Therein, a setup of the test element may be defined by a specific architecture, comprising a defined substrate, a defined geometry, as well as a defined top of the test field including one or more defined test chemicals. Specifically, the test element of the set of test elements may be chosen from the same lot of manufacturing, thereby providing the highest possible degree of identical character of the test elements.

Method step c. comprises applying the test samples to a set of test elements. Thus, as an example, a droplet of the test samples may be applied to the test fields, or the test fields may be wetted by the test samples by other means, such as by dipping the test elements into the test samples. Thereby, as an example, a set of wetted test elements with test samples applied to their test fields is generated, wherein, as an example, at least three test elements are present, having different test samples applied to their respective test fields. As an example, a first test element or a first test field may be provided, having a first test sample applied thereto, a second test element or second test field may be provided, having a second test sample applied thereto, and a third test element or third test field may be provided, having a third test sample applied thereto. Further test samples may be applied to further test elements or test fields. Thereby, the set of test elements, after application of the test samples, may contain a plurality of test fields of the same type, wherein at least three test fields are provided having different test samples applied thereto and, consequently, having different colors after the detection reaction has taken place. Thus, generally, the term "colored test field" specifically may refer to a test field in which, after application of a sample or test sample, the detection reaction has taken place, wherein the color of the test field is determined by the result of the detection reaction.

As further used herein, the term "acquiring images of the colored test fields by using the camera," as used in step d., generally refers to the process of recording at least one image according to the definition given above by using the camera. Therein, specifically, at least one image may be acquired from each of the colored test fields generated in step c. Still, one or more test fields may also be left out. Generally, in step d., a set of images may be created, containing at least one image of at least one first test field having at least one first test sample applied thereto, at least one image of at least one second test field having at least one second test sample applied thereto, and, preferably, at least one further image of at least one further test field, such as at least one image of at least one third test field, having at least one further test sample applied thereto, such as at least one third test sample.

In step e., color coordinates for the images of the colored test fields are generated, by using the color coordinate systems of the set of color coordinate systems, thereby creating a set of color coordinates for the test samples and for the color coordinate systems. Thus, as an example, for each test field wetted by a test sample and, thus, formed into a colored test field, color coordinates according to the color coordinate systems of the set of color coordinate systems may be generated. Specifically, for each of the images of the colored test fields, or for each of at least one image of each of the color test fields, color coordinates may be generated, which each describe the coloration of the respective colored test field. As an example, color coordinates ($F_{i,j}$, $m_{i,j}$, $b_{i,j}$), ($A_{i,j}$, $B_{i,j}$, $C_{i,j}$) or ($A_{i,j}$, $B_{i,j}$, $C_{i,j}$, $D_{i,j}$) may be generated, with i denoting the identity of the color coordinate system of the set of color coordinate systems and j denoting the identity of the colored test field and/or the identity of the test sample. Therein, each of the color coordinate systems of the set of color coordinate systems may be used or a subset containing a selection of color coordinate systems of the set of color coordinate systems may be used. Further, each of the images may be analyzed or a subset of images.

Further, the set of color coordinates for the test samples and for the color coordinate systems may, as an example, contain color coordinates (F, m, b) for each colored test field or test sample in each color coordinate system of the set of color coordinate systems, thus resulting in at least p·q color coordinates, with p being the number of colored test fields or test samples and with q being the number of color coordinates in the set of color coordinate systems, wherein multiple images of a single colored test field may also be taken, thus resulting in an increased number p. Other options are also feasible.

In step f, a set of coding functions is provided, the set of coding functions comprising a plurality of coding functions for transforming color coordinates of a test field into a corresponding concentration of the analyte in the sample.

The term "coding function" as used herein is a broad term and is to be given its ordinary and customary meaning to a person of ordinary skill in the art and is not to be limited to a special or customized meaning. The term specifically may refer, without limitation, to an arbitrary transformation algorithm for transforming color coordinates of a test field, specifically a colored test field wetted by a sample to be analyzed, into a corresponding concentration of the analyte in the sample. For this purpose, the coding functions, as an example, may comprise one or more analytical functions, such as a function transforming one or more or all of the color coordinates measured by a camera taking an image of the colored test field into the concentration of the at least one analyte in the sample. Additionally or alternatively, the coding functions may comprise one or more matrix algorithms or operations for transforming the vector of the color coordinates into the concentration of the at least one analyte. Again, additionally or alternatively, the coding functions may also comprise one or more curves, such as one or more one-dimensional, two-dimensional, three-dimensional or four-dimensional curves for transforming the color coordinates into the concentration of the analyte. Further, additionally or alternatively, the coding functions may also comprise one or more lookup tables or other tables for assigning concentrations of the analyte to respective values or value ranges of the color coordinates.

The set of coding functions, as will be explained in further detail below, specifically may be defined by providing similar functions with one or more parameters to be specified. Thus, specifically, the set of coding functions may be defined by one or more parameters which may be determined for specifying a specific coding function out of the set of coding functions. Examples will be given below.

In step g., the set of color coordinates generated in step e. is transformed into a set of measured concentrations by using the set of coding functions. As used herein, the term "measured concentration" generally may refer to an experimental result indicating a concentration in a sample, based on one or more items of experimental data such as one or more measurement values, in the present case specifically one or more color coordinates. Thus, in step g., the coding functions of the set of coding functions provided in step f are applied to the color coordinates generated in step e. above. Therein, the coding functions may be applied to all of the color coordinates generated in step e., or may be applied to just a subset of these color coordinates generated in step e. Further, all of the coding functions or only a subset of the coding functions of the set of coding functions provided in step f may be applied to the color coordinates. Thus, as an example, in case the coding functions are defined by one or more parameters, only a subset of possible coding functions of the set of coding functions may be applied, such as a subset defined by one or more of a parameter range for one or more or even all of the parameters and/or by a finite number of values for the at least one parameter, such as by subdividing parameter ranges into discrete steps. Generally, in step g., a set of measured concentrations is generated. Thus, as an example, for the plurality of test samples having different concentrations of the analyte, at least one measured concentration may be generated, such as for each of the coding functions of the set of coding functions or for each of the coding functions of the subset of coding functions. As an example, in case n images of colored test fields are evaluated and/or in case n test samples of different concentrations are evaluated by wetting corresponding test fields and generating color coordinates thereof, thereby resulting in n color coordinates or n color coordinate vectors, and in case m coding functions are contained in the set of coding functions or in the subset of coding functions used for evaluation, n·m measured concentrations may be generated instep g.

In step h., the set of measured concentrations is compared with the known concentrations of the test samples of the set of test samples. As used herein, the term "compare" is a broad term and is to be given its ordinary and customary meaning to a person of ordinary skill in the art and is not to be limited to a special or customized meaning. The term specifically may refer, without limitation, to any type of determining a qualitative or quantitative relationship or degree of similarity between at least one first item to be compared and at least one second item to be compared. In the comparison, as an example, at least one item of information indicating a degree of similarity or identity between the at least two items to be compared may be generated. As an example, the at least one item of information indicating the degree of similarity or identity may contain at least one item of statistical information, such as a standard deviation. As an example, the item of statistical information indicating the degree of similarity or identity between the set of measured concentrations and the set of known concentrations may contain the following:

$$\Delta_{i,j} = \sqrt{\Sigma_k (c_M^{i,j,k} - c_K^k)^2}, \qquad (0)$$

with $\Delta_{i,j}$ being a measure for the degree of similarity between the measured concentrations $c_M^j$ for coding function i and color coordinate system j and the corresponding known concentrations $c_K^k$, with k being a number indicating the concentration of the set of test samples. Other types of comparison are generally feasible and are generally known to the skilled person. For graphical representation, as an example, the measured concentrations may be plotted against the concentration of the analyte in the respective test samples, thereby resulting, as an example, in a group of measured concentrations for each known concentration of the respective test samples.

Step h. further comprises determining a best match color coordinate system of the set of color coordinate systems and a best match coding function of the set of coding functions for which the set of measured concentrations best matches with the known concentrations. As used therein, the term "match" is a broad term and is to be given its ordinary and customary meaning to a person of ordinary skill in the art and is not to be limited to a special or customized meaning. The term specifically may refer, without limitation, to the quality of two or more items being similar or identical. Consequently, as used herein, the term "best match" is a broad term and is to be given its ordinary and customary meaning to a person of ordinary skill in the art and is not to be limited to a special or customized meaning. The term specifically may refer, without limitation, to a selection of items from at least two sets of items for which the comparison in the sense of the definition given above indicates the highest degree of similarity or identity, including the option that the items match within a pre-determined range. Thus, as an example, with the formula given above, the best match coding function i* and the best match color coordinate system j* may be the coding function out of the set of coding functions and the color coordinate system out of the set of color coordinates for which the above-mentioned statistical indicator $\Delta_{i,j}$ is minimized. Other means of determining a best match are generally known in the field of statistics and may also be applied in step h.

The result of the calibration method, thus, may be the indication of the best match coding function and the indication of the best match color coordinate system. This result specifically may be camera-specific and may be specific for the type of test element to be used. Consequently, performing the calibration method may be required for each type of camera, such as for each portable device or smartphone having a specific camera, and may be required for each type of test element, such as for each manufacturing lot of the test elements. The calibration method may be performed upfront, such as for each known type of smartphone to be used and for each type of test element to be used and, consequently, the results of the calibration method may already be preprogrammed or provided in a corresponding computer program, such as in a corresponding app to be run on the specific smart phone. The app or computer software may also be configured for detecting the type of smart phone or portable device on which it is run and may select a corresponding coding function and color coordinate system which are known to be best matches for the test element and the camera to be used.

As outlined above, the camera specifically may be a camera of a portable electronic device, such as a camera of a portable computer, e.g., a camera of a notebook computer or a template computer. Specifically, however, the camera may be a camera of a smart phone, since many users carry a smart phone during the day and, thus, the smartphone is an omnipresent measuring device, the use of which for determining analytes such as blood glucose is highly favorable.

As outlined above, the term "set," as used in various instances herein, may generally refer to a finite or infinite number of elements. In the context of the color coordinate systems, as outlined above, the set of color coordinate systems specifically may be defined by a set of parametrized functions for transforming color coordinates, i.e., specifically by one or more of functions having one or more parameters. Specifically, one or more parametrized functions may be used for transforming color coordinates provided by the camera into transformed color coordinates. The transformed color coordinates specifically may be camera-independent transformed color coordinates. Generally, a set of one or more parameters of the parametrized functions may characterize each of the color coordinate systems.

Method step e. for generating color coordinates for the images of the color test fields by using the color coordinate systems of the set of color coordinate systems and creating a set of color coordinates for the test samples and for the coordinate systems may be a single step or may contain multiple substeps. Specifically, the step, firstly, may contain transforming color coordinates for the images as provided by the camera, which typically are camera-dependent, into independent color coordinates. Thus, as an example, the camera may contain a camera chip which creates, after evaluation of the image is recorded with this camera chip, color coordinates (R, G, B) or a quadruple of color coordinates, which generally are dependent on the physical properties of the camera chip, of the optical setup of the camera or of electronics components for recording the image. Thus, as an example, the sensitivity of the camera chip may be dependent on the spectral range. Consequently, the method may contain a method step of transforming the color coordinates provided by the camera into camera-independent color-coordinates, such as color coordinates which avoid the spectral sensitivity of the camera and which are comparable in the sense that, when images of one and the same colored test field are evaluated by different cameras, are, with a given tolerance, identical or at least comparable. Consequently, as used herein, camera-independent color coordinates may be color coordinates which may be obtained from different images taken with different cameras from one and the same colored test field. Therein, generally, standardized camera-independent color coordinate systems may be used, such as CIE coordinates systems. Generally however, as outlined above, method step e. may comprise the following substeps:

e1. generating camera-dependent color coordinates for the images of the colored test field;
e2. transforming the camera-dependent color coordinates into camera-independent color coordinates, by using a first transformation algorithm;
e3. transforming the camera-independent color coordinates into color coordinates for the color coordinate systems of the set of color coordinate systems by using a second transformation algorithm, thereby creating the set of color coordinates for the test samples and for the color coordinate systems.

As used herein, the term "camera-dependent color coordinates" generally refers to color coordinates generated by using a camera for imaging a colored object, wherein the result is dependent on the specific properties of the camera and/or of a camera chip contained therein, such as a CCD and/or CMOS chip. As an example, the camera chip may contain color sensors recording values for each color, such as triples like RGB or quadruples like CMYK, wherein the values are dependent on the sensitivity of the camera chip. Thus, when recording images of one and the same colored object by using different cameras, the camera-dependent color coordinates generated by these cameras may differ.

Thus, generally, step e1. contains evaluating the images of the colored test fields, i.e., of the test fields wetted by the test samples and colored due to the subsequent detection reaction in the test field. As an example, at least one image of each colored test field may be evaluated, for deriving the camera dependent color coordinates thereof, such as each image of each colored test field. Thereby, as an example, a plurality of camera-dependent color coordinates ($R_i$, $G_i$, $B_i$) may be generated, with i being an integer from 1 to p, with p being the number of colored test fields or test samples evaluated.

As further used herein, the term "camera-independent color coordinates" is a broad term and is to be given its ordinary and customary meaning to a person of ordinary skill in the art and is not to be limited to a special or customized meaning. The term specifically may refer, without limitation, to color coordinates which do not, at least to a predetermined tolerance, depend on the sensitivity of the camera or the camera chip. In other words, up to a tolerable discrepancy, camera-independent color coordinates of one and the same object do not depend on the sensitivity of the camera in use.

For performing step e2., a calibration process may be used, or a predetermined calibration function may be applied. As an example, the first transformation algorithm may contain a matrix operation by using a matrix M, specifically a matrix operation for transforming the camera-dependent color coordinates (R, G, B) into camera-independent color coordinates (X, Y, Z) by using the following transformation:

$$(X,Y,Z) = M \cdot (R,G,B). \tag{1}$$

Therein, M may indicate a transformation matrix which may be generated by an independent calibration process. As an example, reference color fields may be used for calibrating the camera and for determining the transformation matrix M and/or the coefficients of this transformation matrix. The camera independent color coordinates X, Y, Z, as an example, may be coordinates based on the perception of the human eye, such as CIE color coordinates. A similar matrix transformation as in equation (1) may also be used in case quadruples of coordinates are used. Matrix transformations of color coordinates are generally known, e.g., from F. König: "Die Charakterisierung von Farbsensoren," Dissertation, Logos Verlag, Berlin, 2001, pp. 48-49.

In step e2., a set of camera-dependent color coordinates ($R_i$, $G_i$, $B_i$), with i=1 ... p and p being the number of colored test fields or test samples evaluated, may be transformed into camera-independent color coordinates ($X_i$, $Y_i$, $Z_i$). Similarly, transformations for quadruples of color coordinates are feasible.

The second transformation algorithm may comprise transforming the camera-independent color coordinates, such as the coordinates X, Y, Z, into the color coordinates of the set of color coordinates by using parametrized functions. Thus, as an example, the second transformation algorithm may comprise transforming the camera-independent color coordinates (X, Y, Z) into the set of color coordinates (F, m, b) by using the following parametrized functions:

$$F = \begin{cases} P_1 * \sqrt[3]{y_r} - P_2 & \text{if } y_r > \varepsilon \\ \kappa y_r & \text{otherwise} \end{cases} \tag{2.1}$$

$$m = P_3 * F(m' - m'_r) \tag{2.2}$$

$$b = P_3 * F(b' - b'_r) \tag{2.3}$$

with:

$$y_r = \frac{Y}{Y_r}$$

$$m' = \frac{P_4 * X}{P_5 * X + P_6 * Y + P_7 * Z}$$

$$b' = \frac{P_8 * X}{P_9 * X + P_{10} * Y + P_{11} * Z}$$

$$m'_r = \frac{P_4 * X}{P_5 * X + P_6 * Y + P_7 * Z}$$

$$b'_r = \frac{P_8 * X}{P_9 * X + P_{10} * Y + P_{11} * Z}$$

and with $P_1$-$P_{11}$ being parameters, specifically real numbers and/or rational numbers.

Therein, in case in step e2., a set of camera-independent color coordinates ($X_i$, $Y_i$, $Z_i$) is generated, with i=1 ... p and p being the number of colored test fields or test samples evaluated, the result of step e3. may be a set of parameterized color coordinates ($F_i$, $m_i$, $b_i$).

The camera-independent color coordinates specifically may be color coordinates based on the sensitivity of the human eye, specifically color coordinates according to a standard, more specifically a CIE standard. Specifically, the camera-independent color coordinates may be tristimulus values.

The second transformation algorithm may also take into account an illumination of the test fields. The second transformation algorithm specifically may take into account the illumination of the test fields, specifically by detecting at least one reference color, specifically a reference color of a white field. Thus, as an example, illumination-dependent color coordinates (F, m, b) may be transformed into relative color coordinates ($F_{rel}$, $m_{rel}$, $b_{rel}$) by using one or more of the following equations:

$$F_{rel} = \frac{F}{F_R} \tag{3.1}$$

$$F_{rel} = \frac{F - F_R}{F_R} \tag{3.2}$$

$$F_{rel} = \frac{F - F_R}{F + F_R} \tag{3.3}$$

$$m_{rel} = \frac{m}{m_R} \tag{3.4}$$

$$m_{rel} = \frac{m - m_R}{m_R} \tag{3.5}$$

$$m_{rel} = \frac{m - m_R}{m + m_R} \tag{3.6}$$

$$b_{rel} = \frac{b}{b_R} \tag{3.7}$$

$$b_{rel} = \frac{b - b_R}{b_R} \tag{3.8}$$

$$b_{rel} = \frac{b - b_R}{b + b_R} \tag{3.9}$$

with ($F_R$, $m_R$, $b_R$) being color coordinates derived from an image of an illuminated reference field.

Thereby, a set of relative color coordinates ($F_{i,\,rel}$, $m_{i,\,rel}$, $b_{i,\,rel}$) may be generated, with i=1 ... p and p being the number of colored test fields or test samples evaluated.

The first transformation algorithm, specifically the matrix M, may be determined in a camera calibration process by acquiring at least one image of at least one reference color field having known camera-independent color coordinates. Thus, as an example, a plurality of reference color fields may be provided, having known camera independent color-coordinates, such as color fields according to a color scale or the like. Images of these reference color fields may be recorded, and, thereby, an equation system may be generated for deriving the coefficients of the matrix M or for any other transformation algorithm. Specifically, again, the known color coordinates of the reference color fields may be known CIE coordinates and/or tristimulus values. Other embodiments, however, are feasible.

As outlined above, in step h., the set of measured concentrations is compared with the known concentrations of the test samples of the set of test samples and the best match color coordinate system of the set of color coordinate systems and a best match coding function of the set of coding functions is determined, for which the set of measured concentrations best matches with the known concentrations. Therein, specifically, step h. may be performed such that, over a predetermined measurement range of concentrations, samples of equidistant concentrations lead to color coordinates in the best match color coordinate system having essentially equidistant color differences. Thus, one of the ideas of photometric coordinate systems like the CIE coordinate system may also be transferred onto the measurement of concentrations. Specifically, over the predetermined measurement range, test samples having different concentrations $c_p$, $c_v$ of the analyte, when applied to the test fields, may result in color coordinates $(F_p, m_p, b_p)$, $(F_v, m_v, b_v)$ of colored test fields with a color difference $$\frac{\Delta E_{p,v}}{\Delta c_{p,v}} = \frac{\sqrt{(F_p - F_v)^2 + (m_p - m_v)^2 + (b_p - b_v)^2}}{|c_p - c_v|} = const. \pm \epsilon, \quad (4)$$

with $\epsilon$ being a predetermined range. The precise value of $\epsilon$ may depend on the chosen color space. As an example, there are color spaces being normalized to the absolute value 100, whereas others may be normalized to the absolute value of 1. In order to give the coordinates F, m and b the same weight, the color coordinates may even be weighted by weighting factors. Generally, $\epsilon$ may be chosen significantly smaller than const, i.e., $\epsilon \ll const$, such as $\epsilon < 0.1 \cdot const$, $\epsilon < 0.01 \cdot const$, $\epsilon < 0.001 \cdot const$ or the like. The precise value of $\epsilon$, generally is not predetermined or required for the method.

The color coordinate system of the set of color coordinate systems and the coding function of the set of coding functions for which the set of measured concentrations best matches with the known concentrations, specifically may form a pair comprising the best match color coordinate system and the best match coding function. This pair specifically may be camera specific and may be provided to a mobile device containing the camera, such as via app or other software.

The set of coding functions, as outlined above, specifically may contain parametrized polynomial functions of the color coordinates. As an example, the parametrized polynomial functions may be selected from the group consisting of:

$$c(F, m, b) = \sum_{i=0}^{N} \sum_{j=0}^{N} \sum_{k=0}^{N} a_{i,j,k} \cdot F^i \cdot m^j \cdot b^k \quad (5)$$

with c(F, m, b) being a measured concentration of the analyte when the colored test field has the color (F, m, b), with N being positive integers, and with $a_{i,j,k}$ being parameters of the polynomial functions. It shall be noted, however, that other types of coding functions may also be used and that, further, the set of coding functions may also contain a mixture of different types of coding functions having parameters therein. The use of polynomial functions, however, simplifies calculations and provides good results for analyte measurements, as will be outlined in further detail below.

As further outlined above, the test elements of the set of test elements used in step c. specifically may be of the same type, such as by being all identical, specifically from the setup. Specifically, these test elements may be of the same manufacturing lot. The calibration method may further comprise defining at least one standard test element set up, the standard test element set up defining at least one type of test chemical for the at least one test field comprising at least one test chemical configured for performing an optically detectable detection reaction with the analyte. The standard test element setup may further comprise a defined substrate onto which the test chemical is applied.

As outlined above, the set of test samples specifically may comprise at least three different test samples providing at least three different concentrations of the analyte. Specifically, the concentrations may be distributed equidistantly over a measurement range. The analyte specifically may be glucose. As outlined above, however, other types of analytes may also be detected. The samples specifically may be a bodily fluid, such as blood or interstitial fluid. It shall be noted, however, that other types of samples are also feasible. The set of test samples may contain test samples of different concentrations over a predetermined measurement range of 0 mg/dl to 600 mg/dl. Thus, as an example, for samples of blood or interstitial fluid and glucose being the analyte, the measurement range may be 0 mg/dl to 600 mg/dl, and the concentrations of the test samples may be distributed over the measurement range, such as equidistantly.

As will be outlined in further detail below, the calibration method specifically may be performed by using a computer or computer network. Thus, specifically, at least one of steps a., d., e., f., g., or h. may be performed by using a computer or computer network and/or may be encoded in software.

In a further aspect of this disclosure, a detection method for detecting an analyte in a sample is disclosed. As will be outlined in further detail below, the method makes use of the calibration method as discussed above. Consequently, for possible definitions and embodiments, reference may be made to the disclosure given above or given in further detail below. The method comprises the following steps which specifically may be performed in the given order. Still, a different order is also possible. It is further possible to perform two or more of the method steps fully or partially simultaneously. It is further possible to perform one or more method steps or even all of the method steps once or repeatedly. The method may comprise additional method steps which are not listed herein. Generally, the method for detecting the analyte in the sample comprises the following steps:

A. providing a camera;
B. calibrating the camera by using the calibration method;
C. applying the sample to a test element, the test element having at least one test field comprising at least one test chemical configured for performing an optically detectable detection reaction with the analyte, thereby creating at least one colored test field for the sample;

D. acquiring at least one image of the at least one colored test field;

E. generating color coordinates of the test field by using the best match color coordinate system;

F. transforming the color coordinates into a measurement concentration of the analyte in the sample by using the best match coding function.

As for method steps A. and B., reference may be widely made to the description of the calibration method as given above. For method step C., the step may be performed in a widely analogous fashion to method step c. above, except for the fact that, generally, the sample and the content of the analyte therein is unknown. The test element used in method step C. specifically may be identical or of the same type, preferably of the same manufacturing lot, as the test element used in method step c. above. Due to the detection reaction in the presence of the analyte to be detected, the test field of the test element turns into a colored test field, depending, as an example, on the concentration of the analyte in the sample, including the possibility that no analyte is present in the sample. Generally, one or more test fields may be wetted by the at least one sample.

For method step D., reference may be made to the description of method step d. above. The acquisition of an image in method step D. may take place in a similar way.

As for method steps E. and F., the best match color coordinate system and the best match coding functions as determined in step h. above are used. Again, generating the color coordinates of the test field may be a single step process or maybe a multiple step process. In the latter case, as an example, the camera, firstly, may generate camera-dependent color coordinates for the test field, such as (R, G, B), in an analogous fashion to step e1 above. These camera-dependent color coordinates may then be transformed into camera-independent color coordinates, wherein reference may be made to the description of step e2. above. Thus, for example, camera-independent coordinates (X, Y, Z) may be generated for the colored test field. Further, the camera-independent color coordinates may then be transformed into the color coordinates of the best match color coordinates system, such as into (F, m, b), e.g., by using one or more of equations (2.1-2.3) or (3.1-3.6) above, with the best match set of parameters P. Subsequently, in step F., the color coordinates may then be transformed into the measured concentration of the analyte, e.g., by using equation (5) above, with the best match parameters.

Specifically, steps C.-F. may be performed repeatedly. Step B. may be performed either only once initially for a plurality of repetitions of steps C.-F. or each time before performing steps C.-F.

As outlined above, the test element used in step C. may specifically be of the same type as the test elements of the set of test elements in step c. of the calibration method. Thus, the test element may have the same setup as used for the calibration method or may be manufactured in the same lot.

Again, the detection method may be supported by a computer or a computer network, such as a computer or a computer network of a portable device, such as one or more of a tablet, a notebook or a cell phone such as a smart phone. Specifically, a computer or computer network may be used for performing one or more of steps B., D., E., or F.

Further disclosed and proposed herein is a computer program including computer-executable instructions for performing the method according to this disclosure in one or more of the embodiments enclosed herein when the program is executed on a computer or computer network. Thus, as outlined above, the computer program specifically may contain computer-executable instructions for performing one or more or even all of the steps of the calibration method. Specifically, the computer program may contain computer-executable instructions for performing one or more or even all of the steps a., d., e., f., g., or h. of the calibration method. Additionally or alternatively, a computer program with computer executable-instructions for performing at least some or even all of the method steps of the detection method is proposed, such as one or more or even all of steps B., D., E., or F. of the detection method. Specifically, the computer program may be stored on a computer-readable data carrier.

Further disclosed and proposed herein is a computer program product having program code means, in order to perform the method according to this disclosure in one or more of the embodiments enclosed herein, such as one or more of the method steps described above in the context of the computer program, when the program is executed on a computer or computer network. Specifically, the program code means may be stored on a computer-readable data carrier.

Further disclosed and proposed herein is a data carrier having a data structure stored thereon, which, after loading into a computer or computer network, such as into a working memory or main memory of the computer or computer network, may execute the method according to one or more of the embodiments disclosed herein, such as by executing one or more of the above-mentioned steps discussed in the context of the computer program.

Further disclosed and proposed herein is a computer program product with program code means stored on a machine-readable carrier, in order to perform the method according to one or more of the embodiments disclosed herein, when the program is executed on a computer or computer network, such as one or more of the above-mentioned steps discussed in the context of the computer program. As used herein, a computer program product refers to the program as a tradable product. The product may generally exist in an arbitrary format, such as in a paper format, or on a computer-readable data carrier. Specifically, the computer program product may be distributed over a data network.

Finally, disclosed and proposed herein is a modulated data signal which contains instructions readable by a computer system or computer network, for performing the method according to one or more of the embodiments disclosed herein, such as one or more of the above-mentioned steps discussed in the context of the computer program.

Referring to the computer-implemented aspects of this disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, further disclosed herein are:

a computer or computer network comprising at least one processor, wherein the processor is adapted to fully or partially perform one of the methods according to one of the embodiments described in this description, a computer loadable data structure that is adapted to fully or partially perform one of the methods according to one of the embodiments described in this description while the data structure is being executed on a computer, a computer program, wherein the computer program is adapted to fully or partially perform one of the methods according to one of the embodiments described in this description while the program is being executed on a computer, a computer program comprising program means for fully or partially performing one of the methods according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to fully or partially perform one of the methods according to one of the embodiments described in this description after having been loaded into a main and/or working storage of a computer or of a computer network, and a computer program product having program code means, wherein the program code means can be stored or are stored on a storage medium, for fully or partially performing one of the methods according to one of the embodiments described in this description, if the program code means are executed on a computer or on a computer network.

In a further aspect of this disclosure, a calibration system for calibrating a camera is disclosed, for the purpose of detecting an analyte in a sample by using the camera. The calibration system comprises at least one computer or computer network. The calibration system is configured for performing the calibration method according to this disclosure in any one of the embodiments described herein, such as by appropriate software programming of the computer or computer network. Further, the calibration system may comprise a set of test samples having known concentrations of the analyte and a set of test elements, each test element having at least one test field. Further, the calibration system may comprise the camera.

In a further aspect of this disclosure, a detection system is disclosed, for the purpose of detecting an analyte in a sample by using at least one test element having at least one test field comprising at least one test chemical configured for performing an optically detectable detection reaction with the analyte. The detector system comprises at least one camera, such as a camera of a mobile device, e.g., of a smart phone. The detector system further comprises at least one computer or computer network, specifically at least one smart phone. The detection system is configured for performing the detection method according to any one of the embodiments described herein. Further, the detection system may comprise at least one sample and at least one test element, the test element having at least one test field. Further, the detection system may comprise a set of test samples having known concentrations of the analyte and a set of test elements, each test element having at least one test field. Further, a computer program is disclosed comprising instructions, which when the computer program is executed by the calibration system as described above or as will further be described below in more detail or by the detection system as described above or as will further be described below in more detail, cause the calibration system as described above or as will further be described below in more detail or the detection system as described above or as will further be described below in more detail to carry out the steps of the calibration method as described above or as will further be described below in more detail or of the detection method as described above or as will further be described below in more detail, respectively.

In a further aspect of this disclosure, a computer program is disclosed comprising instructions which, when the computer program is executed by a computer or computer network, causes the computer or the computer network to carry out at least one of steps a., d., e., f., g. or h. of the calibration method or one or more of steps B., D., E. or F. of the detection method as described above or as will further be described below in more detail.

In a further aspect of this disclosure, a system for detecting an analyte in a sample is disclosed. The system comprises the calibration system and the detection system according to this disclosure.

The methods, computer programs and systems according to the present application may provide a large number of advantages over known applications for calibrating and/or using a camera for detecting an analyte in a sample. Thus, in particular, this disclosure may improve an accuracy of a determination of an analyte concentration value. Particularly, the present application may provide a specifically adapted color space used in the algorithm for determining an analyte concentration in a sample, for example, for determining a blood glucose concentration. Specifically, the present application may provide a specifically adapted color space creating a linear relationship between a color of the test strip and an analyte concentration, specifically a linear relationship between the color of the test strip and a resulting numerical representation thereof. The linear relationship of the adapted color space may achieve a uniform accuracy over the complete range of measurement values. Further, the present application may alternatively allow a particularly high accuracy of the determination of the analyte concentration within a defined range of measurement values, particularly within a predefined range of measurement values.

Further, the present application may improve a validity of an optical determination of an analyte concentration value. Specifically, a validity of an optical measurement may be improved compared to applications known from the art. In particular, the specifically adapted color space provided in the present application may be based on externally determined analyte concentrations. More particularly, the present methods, computer programs and systems may provide the specifically adapted color space by optimizing and adapting the color space to the externally determined analyte concentration, for example analyte concentrations determined in a laboratory, specifically allowing a particularly high validity of the determined analyte concentration, thus improving the validity of the optically determined analyte concentration using the adapted color space. In contrast thereto, prior art usually aims at optimization based on human color perception.

Furthermore, non-linear factors having an impact on the detection of the analyte in the sample may be taken into account in the methods, computer programs and systems according to the present application, as opposed to other methods known by prior art. Thus, the impact on the detection of the analyte in the sample by non-linear factors may be minimized or even erased by the present application. Specifically, non-linear factors such as different or changeable lighting conditions or individual technical and optical properties of a huge number of cameras available on the market may be taken into account in the methods, computer programs and systems according to the present application.

Summarizing and without excluding further possible embodiments, the following embodiments may be envisaged:

Embodiment 1

A calibration method for calibrating a camera for detecting an analyte in a sample, comprising:
a. providing a set of color coordinate systems, the set of color coordinate systems comprising a plurality of different color coordinate systems configured for describing a color of an object;
b. providing a set of test samples having known concentrations of the analyte;
c. applying the test samples to a set of test elements, each test element having at least one test field comprising at least one test chemical configured for performing an optically detectable detection reaction with the analyte, thereby creating at least one colored test field for each of the test samples;
d. acquiring images of the colored test fields by using the camera;
e. generating color coordinates for the images of the colored test fields, by using the color coordinate systems of the set of color coordinate systems, thereby creating a set of color coordinates for the test samples and for the color coordinate systems;
f. providing a set of coding functions, the set of coding functions comprising a plurality of coding functions for transforming color coordinates of a test field into a corresponding concentration of the analyte in the sample;
g. transforming the set of color coordinates generated in step e. into a set of measured concentrations by using the set of coding functions; and
h. comparing the set of measured concentrations with the known concentrations of the test samples of the set of test samples and determining a best match color coordinate system of the set of color coordinate systems and a best match coding function of the set of coding functions for which the set of measured concentrations best matches with the known concentrations.

Embodiment 2

The calibration method according to the preceding embodiment, wherein the camera is a smart phone camera.

Embodiment 3

The calibration method according to any one of the preceding embodiments, wherein the set of color coordinate systems is defined by a set of parametrized functions for transforming color coordinates, specifically for transforming color coordinates provided by the camera into transformed color coordinates, more specifically into camera-independent transformed color coordinates, wherein a set of parameters of the parametrized functions characterizes each of the color coordinate systems.

Embodiment 4

The calibration method according to any one of the preceding embodiments, wherein step e. comprises:

e1. generating camera-dependent color coordinates for the images of the colored test field;
e2. transforming the camera-dependent color coordinates into camera-independent color coordinates, by using a first transformation algorithm;
e3. transforming the camera-independent color coordinates into color coordinates for the color coordinate systems of the set of color coordinate systems by using a second transformation algorithm, thereby creating the set of color coordinates for the test samples and for the color coordinate systems.

Embodiment 5

The calibration method according to the preceding embodiment, wherein the first transformation algorithm contains a matrix operation by using a matrix M, specifically a matrix operation for transforming the camera-dependent color coordinates (R, G, B) into camera-independent color coordinates (X, Y, Z) by using the following transformation:

$$(X, Y, Z) = M \cdot (R, G, B). \tag{1}$$

Embodiment 6

The calibration method according to any one of the two preceding embodiments, wherein the second transformation algorithm comprises transforming the camera-independent color coordinates into the color coordinates of the set of color coordinates by using parametrized functions.

Embodiment 7

The calibration method according to the preceding embodiment, wherein the second transformation algorithm comprises transforming the camera-independent color coordinates (X, Y, Z) into the set of color coordinates (F, m, b) by using the following parametrized functions:

$$F = \begin{cases} P_1 * \sqrt[3]{y_r} - P_2 & \text{if } y_r > \varepsilon \\ \kappa y_r & \text{otherwise} \end{cases} \tag{2.1}$$

$$m = P_3 * F(m' - m'_r) \tag{2.2}$$

$$b = P_3 * F(b' - b'_r) \tag{2.3}$$

with:

$$y_r = \frac{Y}{Y_r}$$

$$m' = \frac{P_4 * X}{P_5 * X + P_6 * Y + P_7 * Z}$$

$$b' = \frac{P_8 * X}{P_9 * X + P_{10} * Y + P_{11} * Z}$$

$$m'_r = \frac{P_4 * X}{P_5 * X + P_6 * Y + P_7 * Z}$$

$$b'_r = \frac{P_8 * X}{P_9 * X + P_{10} * Y + P_{11} * Z}$$

and with $P_1$-$P_{11}$ being parameters, specifically real numbers and/or rational numbers.

Embodiment 8

The calibration method according to any one of the four preceding embodiments, wherein the second transformation algorithm takes into account an illumination of the test fields.

Embodiment 9

The calibration method according to any one of the five preceding embodiments, wherein the camera-independent color coordinates are color coordinates based on the sensitivity of the human eye, specifically color coordinates according to a standard, more specifically a CIE standard.

Embodiment 10

The calibration method according to the preceding embodiment, wherein the camera-independent color coordinates are tristimulus values.

Embodiment 11

The calibration method according to the preceding embodiment, wherein the second transformation algorithm takes into account the illumination of the test fields, specifically by detecting at least one reference color, specifically a reference color of a white field.

Embodiment 12

The calibration method according to the preceding embodiment, wherein illumination-dependent color coordinates (F, m, b) are transformed into relative color coordinates ($F_{rel}$, $m_{rel}$, $b_{rel}$) by using one or more of the following equations:

$$F_{rel} = \frac{F}{F_R} \quad (3.1)$$

$$F_{rel} = \frac{F - F_R}{F_R} \quad (3.2)$$

$$F_{rel} = \frac{F - F_R}{F + F_R} \quad (3.3)$$

$$m_{rel} = \frac{m}{m_R} \quad (3.4)$$

$$m_{rel} = \frac{m - m_R}{m_R} \quad (3.5)$$

$$m_{rel} = \frac{m - m_R}{m + m_R} \quad (3.6)$$

with ($F_R$, $m_R$, $b_R$) being color coordinates derived from an image of an illuminated reference field.

Embodiment 13

The calibration method according to any one of the nine preceding embodiments, wherein the first transformation algorithm, specifically the matrix M, is determined in a camera calibration process by acquiring at least one image of at least one reference color field having known camera-independent color coordinates, specifically known CIE coordinates and/or tristimulus values.

Embodiment 14

The calibration method according to any one of the preceding embodiments, wherein step h. is performed such that, over a predetermined measurement range of concentrations, samples of equidistant concentrations lead to color coordinates in the best match color coordinate system having essentially equidistant color differences.

Embodiment 15

The calibration method according to the preceding embodiment, wherein, over the predetermined measurement range, test samples having different concentrations $c_p$, $c_v$ of the analyte, when applied to the test fields, result in color coordinates ($F_p$, $m_p$, $b_p$), ($F_v$, $m_v$, $b_v$) of colored test fields with a color difference $$\frac{\Delta E_{p,v}}{\Delta c_{p,v}} = \frac{\sqrt{(F_p - F_v)^2 + (m_p - m_v)^2 + (b_p - b_v)^2}}{|c_p - c_v|} = const. \pm \epsilon, \quad (4)$$

with $\epsilon$ being a predetermined range.

Embodiment 16

The calibration method according to any one of the preceding embodiments, wherein the color coordinate system of the set of color coordinate systems and the coding function of the set of coding functions for which the set of measured concentrations best matches with the known concentrations form a pair comprising the best match color coordinate system and the best match coding function.

Embodiment 17

The calibration method according to any one of the preceding embodiments, wherein the set of coding functions contains parametrized polynomial functions of the color coordinates.

Embodiment 18

The calibration method according to the preceding embodiment, wherein the parametrized polynomial functions are selected from the group consisting of:

$$c(F, m, b) = \sum_{i=0}^{N} \sum_{j=0}^{N} \sum_{k=0}^{N} a_{i,j,k} \cdot F^i \cdot m^j \cdot b^k \quad (5)$$

with c(F, m, b) being a measured concentration of the analyte when the colored test field has the color (F, m, b), with N being positive integers, and with $a_{i,j,k}$ being parameters of the polynomial functions.

Embodiment 19

The calibration method according to any one of the preceding embodiments, wherein the test elements of the set of test elements used in step c. all are of the same type, preferably all are identical.

Embodiment 20

The calibration method according to any one of the preceding embodiments, wherein the method further comprises defining at least one standard test element set up, the standard test element set up defining at least one type of test chemical for the at least one test field comprising at least one test chemical configured for performing an optically detectable detection reaction with the analyte.

Embodiment 21

The calibration method according to the preceding embodiment, wherein the standard test element setup further comprises a defined substrate onto which the test chemical is applied.

Embodiment 22

The calibration method according to any one of the preceding embodiments, wherein the set of test samples comprises at least three different test samples providing at least three different concentrations of the analyte.

Embodiment 23

The calibration method according to any one of the preceding embodiments, wherein the analyte is glucose.

Embodiment 24

The calibration method according to the preceding embodiment, wherein the sample is a bodily fluid.

Embodiment 25

The calibration method according to any one of the two preceding embodiments, wherein the set of test samples contains test samples of different concentrations over a predetermined measurement range of 0 mg/dl to 600 mg/dl.

Embodiment 26

The calibration method according to any one of the preceding embodiments, wherein the calibration method is performed by using a computer or computer network, specifically for performing at least one of steps a., d., e., f, g., or h.

Embodiment 27

A detection method for detecting an analyte in a sample, the method comprising:
A. providing a camera;
B. calibrating the camera by using the calibration method according to any one of the preceding embodiments;
C. applying the sample to a test element, the test element having at least one test field comprising at least one test chemical configured for performing an optically detectable detection reaction with the analyte, thereby creating at least one colored test field for the sample;
D. acquiring at least one image of the at least one colored test field;
E. generating color coordinates of the test field by using the best match color coordinate system; and
F. transforming the color coordinates into a measurement concentration of the analyte in the sample by using the best match coding function.

Embodiment 28

The detection method according to the preceding embodiment, wherein the test element used in step C. is of the same type as the test elements of the set of test elements in step c. of the calibration method.

Embodiment 29

The detection method according to any one of the preceding embodiments referring to a detection method, wherein steps C.-F. are performed repeatedly, wherein step B. is performed either only once initially for a plurality of repetitions of steps C.-F. or each time before performing steps C.-F.

Embodiment 30

The detection method according to any one of the preceding embodiments referring to a detection method, wherein the detection method is performed by using a computer or computer network, specifically for performing one or more of steps B., D., E., or F.

Embodiment 31

A computer program comprising instructions which, when the computer program is executed by a computer or computer network, causes the computer or computer network to carry out the steps of the calibration method according to any one of the preceding embodiments referring to a calibration method or of the detection method according to any one of the preceding embodiments referring to a detection method.

Embodiment 32

A calibration system for calibrating a camera for the purpose of detecting an analyte in a sample by using the camera, the calibration system comprising at least one computer or computer network, the calibration system being configured for performing the calibration method according to any one of the preceding embodiments referring to a calibration method.

Embodiment 33

The calibration system according to the preceding embodiment, wherein the calibration system further comprises a set of test samples having known concentrations of the analyte and a set of test elements, each test element having at least one test field.

Embodiment 34

The calibration system according to any one of the two preceding embodiments, wherein the calibration system further comprises the camera.

Embodiment 35

A detection system for detecting an analyte in a sample by using at least one test element having at least one test field comprising at least one test chemical configured for performing an optically detectable detection reaction with the analyte, the detection system comprising at least one camera, specifically a camera of a smart phone, the detection system further comprising at least one computer or computer network, specifically at least one smart phone, the detection system being configured for performing the detection method according to any one of the preceding embodiments referring to a detection method.

Embodiment 36

The detection system according to the preceding embodiment, wherein the detection system further comprises at least one sample and at least one test element, the test element having at least one test field.

Embodiment 37

The detection system according to any one of the two preceding embodiments, wherein the detection system further comprises a set of test samples having known concentrations of the analyte and a set of test elements, each test element having at least one test field.

Embodiment 38

A system for detecting an analyte in a sample, comprising the calibration system and the detection system according to the two preceding embodiments.

BRIEF DESCRIPTION OF THE DRAWINGS

Further optional features and embodiments will be disclosed in more detail in the subsequent description of embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements. The above-mentioned aspects of exemplary embodiments will become more apparent and will be better understood by reference to the following description of the embodiments taken in conjunction with the accompanying drawings, wherein:

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
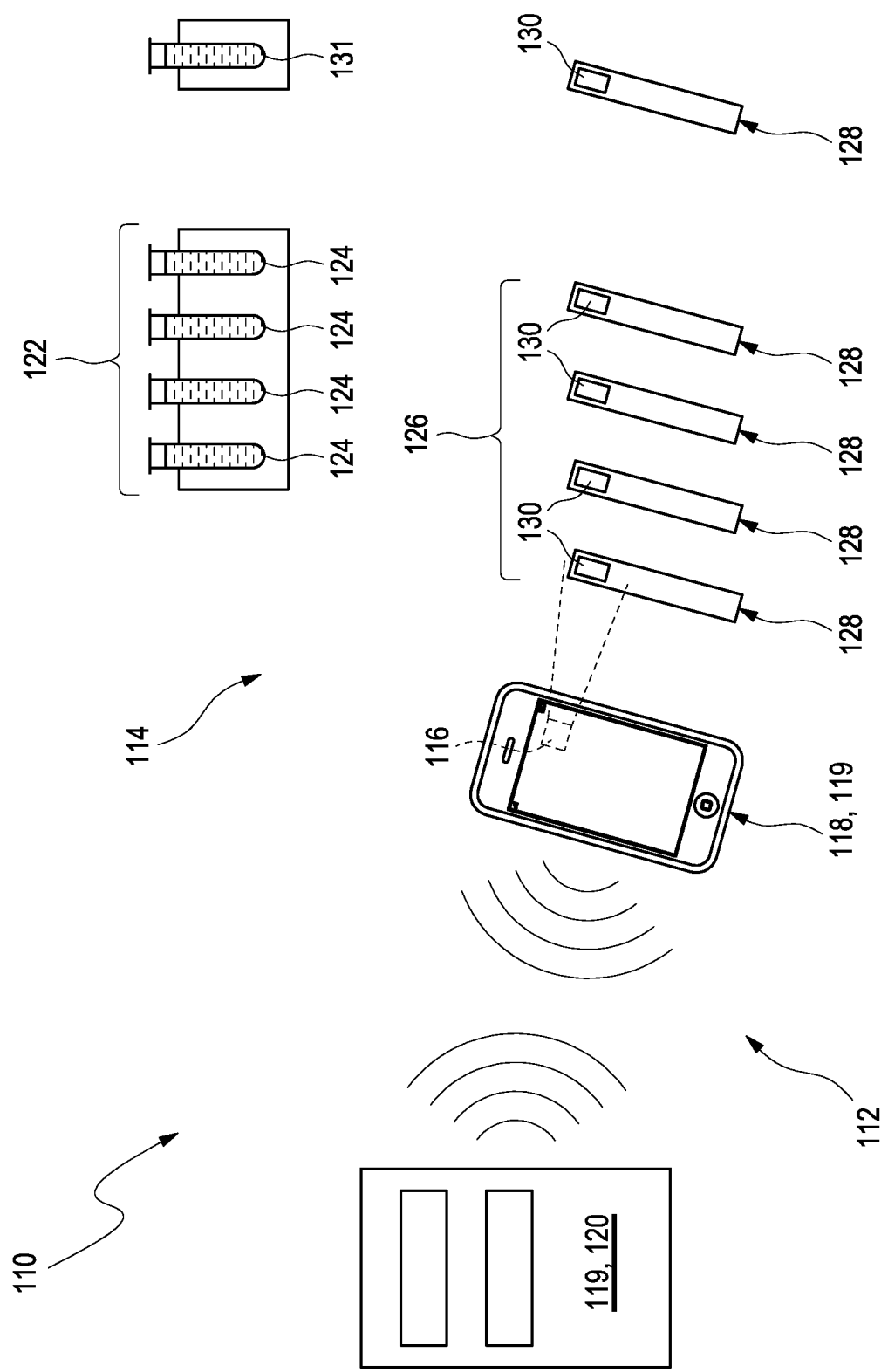
FIG. 1 illustrates an embodiment of a system, an embodiment of a detection system and an embodiment of a calibration system.
Figure 2:
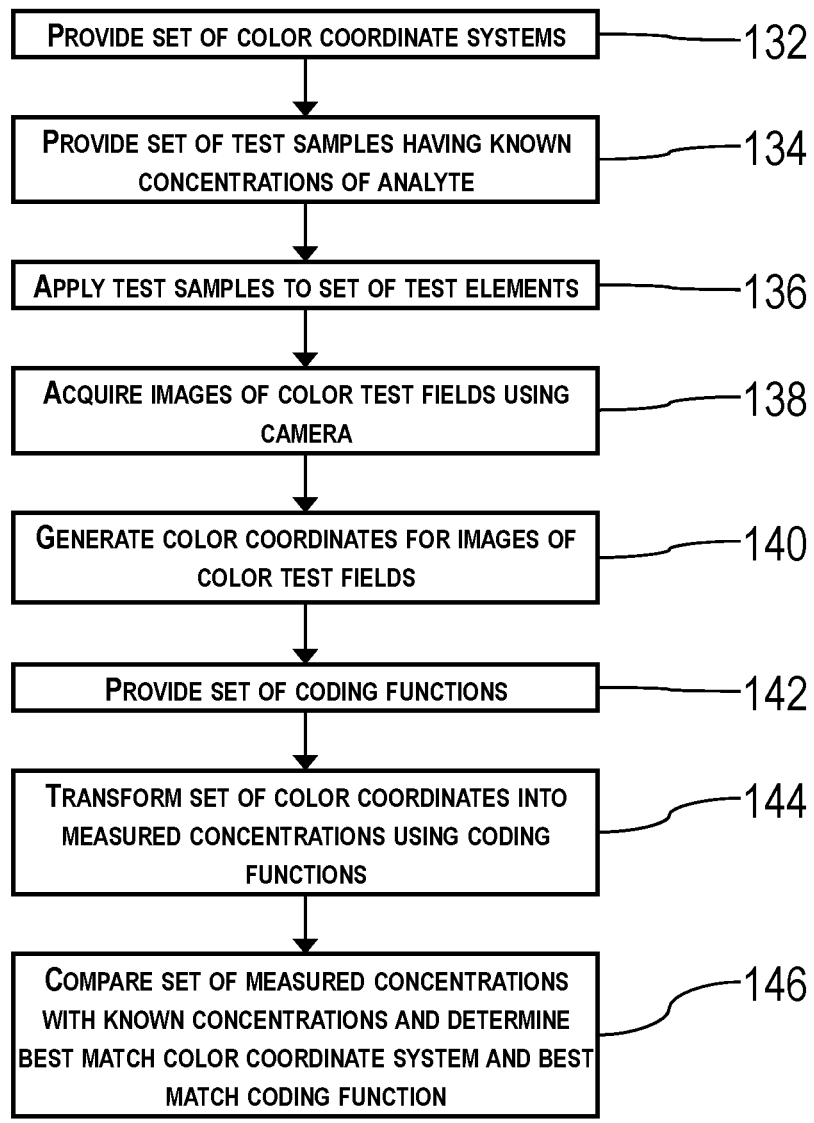
FIGS. 2 and 3 illustrate embodiments of a flow chart of a calibration method.
Figure 3:
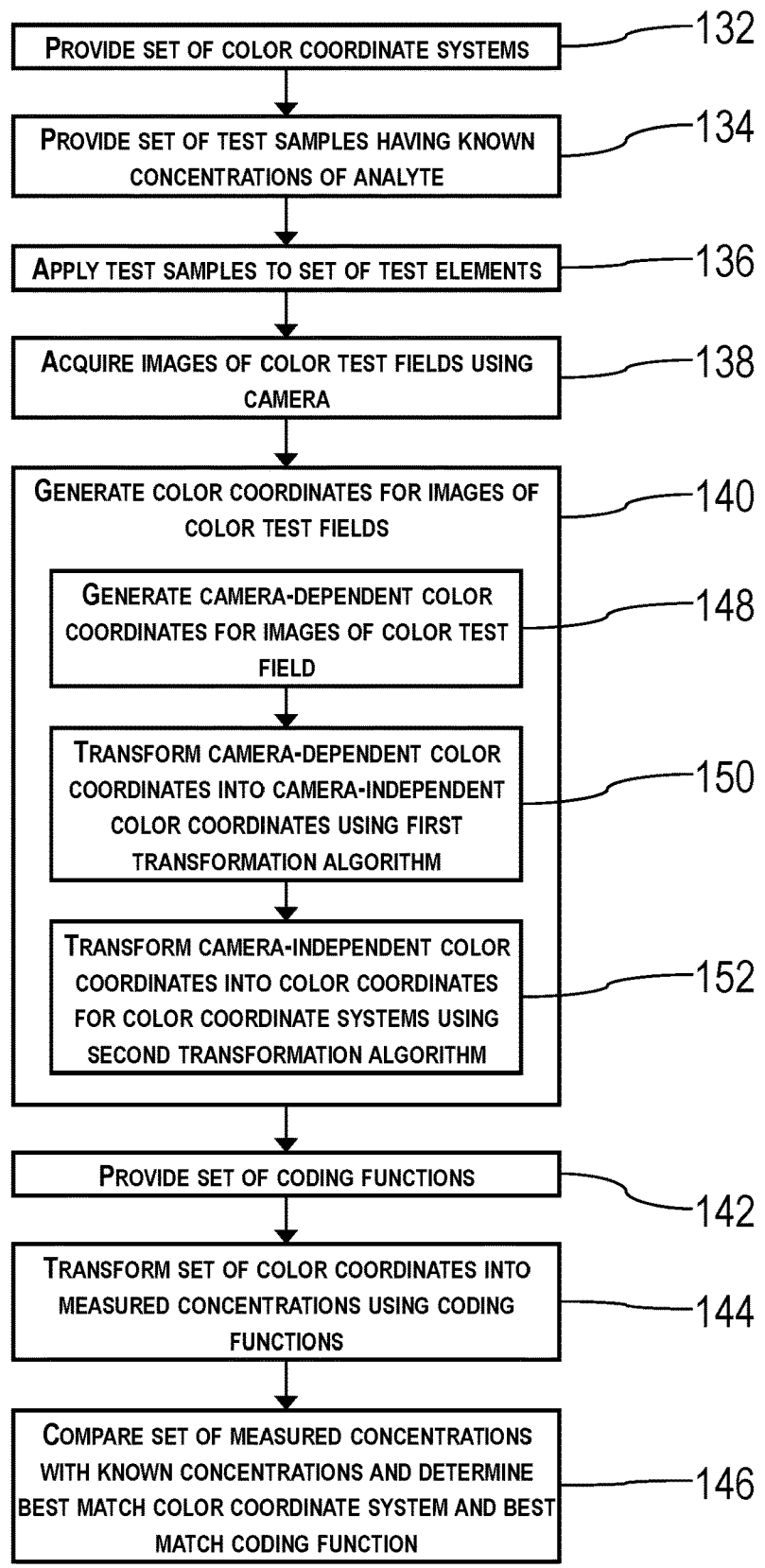

An embodiment of a system 110 is illustrated in FIG. 1, the system 110 having a calibration system 112 and a detection system 114. The calibration system 112, as illustrated in FIG. 1, is configured for calibrating a camera 116, for example a camera comprised by a smart phone 118. The calibration system 112 comprises at least one computer 119 or computer network 120. In the illustrated embodiment of the calibration system 112, the computer 119 may specifically be a stationary computer or computer network 120. Alternatively, the computer 119 may for example be a computer network of a mobile or portable device, such as one or more of a tablet, a notebook or a cell phone such as, for example, a smart phone 118. The calibration system 112 is further configured for performing a calibration method, specifically the calibration method as illustrated in FIGS. 2 and 3. Further, FIG. 1 illustrates a set of test samples 122, specifically a set of test samples 122 comprising more than one test sample 124. The test samples 124 may specifically be samples of a bodily fluid, such as for example blood or urine. The test samples 124 comprised by the set of test samples 122 may specifically have different concentrations of an analyte. Particularly, each test sample 124 may have a known concentration of the analyte, specifically, when calibrating the camera 116. Further, FIG. 1 illustrates a set of test elements 126, each test element 128 having at least one test field 130 comprising at least one test chemical configured for performing an optically detectable detection reaction with the analyte, thereby creating at least one colored test field 130.

Figure 4:
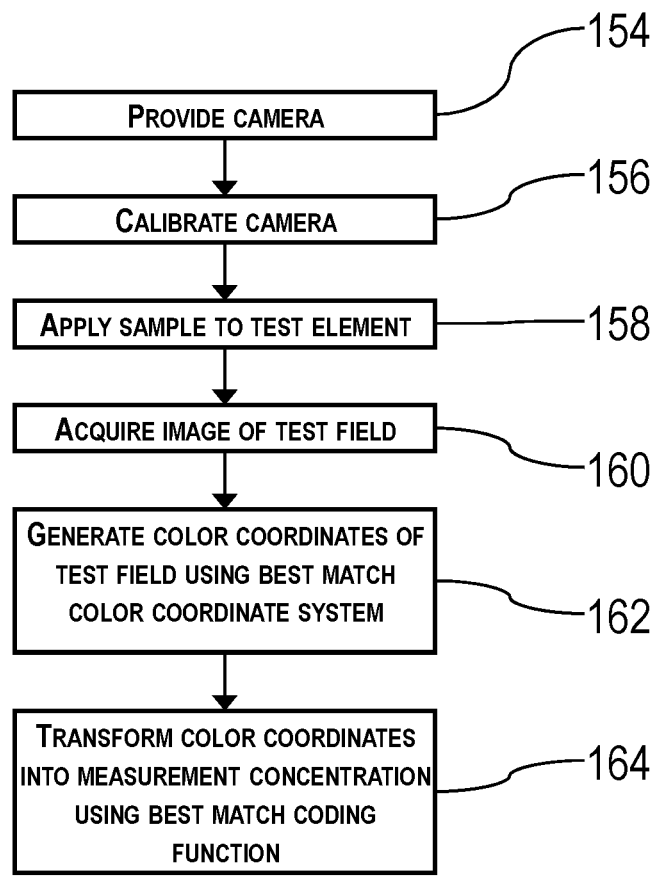
FIG. 4 illustrates an embodiment of a flow chart of a detection method.

The detection system 114, as illustrated in FIG. 1, is configured for detecting an analyte in a sample 131 by using at least one test element 128 having at least one test field 130. The sample 131 may for example be a single sample for the purpose of detecting the analyte concentration, thus, in particular, the concentration of the analyte within the sample 131 may be unknown. Specifically, the detection system 114 may be configured for detecting the analyte in the sample 131 as illustrated separately from the set of test samples 122 in FIG. 1. Similarly, the test element 128 having the test field 130 may be the test element 128 as illustrated separately from the set of test elements 126 in FIG. 1. The test field 130 comprises at least one test chemical configured for performing an optically detectable detection reaction with the analyte. The detection system 114 comprises at least one camera 116, specifically a camera 116 of a smart phone 118. Further, the detection system 114 comprises at least one computer 119 or computer network 120. In the illustrated embodiment of the detection system 114, the computer 119 may specifically be a smart phone 118. The detection system is further configured for performing a detection method, specifically the detection method as illustrated in FIG. 4.

In general, typical difficulties may occur when calibrating a camera for detecting optical detectable detection reactions. As an example, an approach to determine a measuring unit for measuring a color difference used for calibrating the camera may comprise the following three steps.

The first step may, for example, comprise performing an initial transformation. Specifically, the first step may comprise transforming camera-dependent color coordinates, e.g., (R, G, B), into camera-independent color coordinates, such as for example (X, Y, Z). Exemplarily, the initial transformation may serve the purpose of connecting a physical size of an electromagnetic spectrum and a physiological color vision. For example, the initial transformation may make use of equation (1) as disclosed in the description above. Specifically, standard algorithms, for example standard algorithms based on a measurement of a reference color, may be used for determining the transformation matrix M used in equation (1). Again, reference may be made to F. König: "Die Charakterisierung von Farbsensoren," Dissertation, Logos Verlag, Berlin, 2001, pp. 48-49.

The second step may comprise a further transformation. Specifically, the second step may comprise transforming the camera-independent color coordinates, e.g., (X, Y, Z), into a chosen color space, such as a color space suitable for optimizing color differences for example color differences according to human color perception, for example a color space in accordance with the CIE. The following equations exemplarily show a calculation of the transformation of the camera-independent color coordinates into the CIE L*a*b* color space.

$$L^* = 116 f_y - 16 \quad (6.1)$$

$$a^* = 500(f_x - f_y) \quad (6.2)$$

$$b^* = 200(f_y - f_z) \quad (6.3)$$

wherein:

$$f_x = \begin{cases} \sqrt[3]{x_r} & \text{if } x_r > \epsilon \\ \frac{\kappa x_r + 16}{116} & \text{otherwise} \end{cases} ; \text{with } x_r = \frac{X}{X_r}$$

$$f_y = \begin{cases} \sqrt[3]{y_r} & \text{if } y_r > \epsilon \\ \frac{\kappa y_r + 16}{116} & \text{otherwise} \end{cases} ; \text{with } y_r = \frac{Y}{Y_r}$$

$$f_z = \begin{cases} \sqrt[3]{z_r} & \text{if } z_r > \epsilon \\ \frac{\kappa z_r + 16}{116} & \text{otherwise} \end{cases} ; \text{with } z_r = \frac{Z}{Z_r}$$

$$\epsilon = 0.008856; \kappa = 903.3$$

The third step may comprise calculating and/or defining a measuring unit for measuring a difference between colors, e.g., a color difference. For example, a color difference, such as a color difference between two samples p and v, based on the L*a*b* color space may be determined using the following equation:

$$= \sqrt{(L_p^* - L_v^*)^2 + (a_p^* - a_v^*)^2 + (b_p^* - b_v^*)^2} \, \Delta E_{p,v} \quad (7)$$

In particular, other mathematical expressions or equations for defining measuring units may be used, such as non-linear equations, for example, more complex non-linear equations taking into account possible non-linear effects on the color difference. Specifically, non-linear equations taking into account a possible effect of ambient brightness on the color difference, e.g., $\Delta E_{94}$ and $\Delta E_{00}$, may be used for determining the measuring unit for measuring the color difference.

The above-mentioned methods typically imply several challenges when applied to analytical measurements. Thus, it should be considered that mathematical expressions, e.g., mathematical expressions for defining measuring units, based on CIE recommendations, may aim at establishing a connection or relation between human color perception and physical origins of color stimulus and may therefore lead to irregular or non-linear representations of equidistant data, such as for example of equidistant analyte concentrations. In particular, said non-linear representations may for example lead to a non-linear or irregular accuracy of a determined analyte concentration when used for calibrating the camera 116 for detecting the analyte. Thus, a calibration method for calibrating the camera 116 for detecting the analyte in the sample 131 according to this disclosure may particularly be performed such that, over a predetermined measurement range of concentrations, samples of equidistant concentrations lead to color coordinates having essentially equidistant color differences. An embodiment of a flow chart of the calibration method for calibrating the camera 116 for detecting the analyte in the sample 131 is illustrated in FIG. 2.

In FIG. 2, a calibration method according to this disclosure is shown. The calibration method illustrated in FIG. 2 comprises step a. (method step 132) for providing a set of color coordinate systems, the set of color coordinate systems comprising a plurality of different color coordinate systems configured for describing a color of an object. The calibration method further comprises step b. (method step 134) for providing a set of test samples 122 having known concentrations of the analyte. Specifically, the set of test samples 122 illustrated in FIG. 1 may be provided.

Further, the calibration method comprises step c. (method step 136) for applying the test samples 124 to a set of test elements 126. Specifically, the test samples 124 may be applied to a set of test elements 126, illustrated in FIG. 1. In particular, each of the test samples 124 from the set of test samples 122 may be applied to a test element 128 from the set of test elements 126 respectively. Each test element 128 having at least one test field 130 comprising at least one test chemical configured for performing an optically detectable detection reaction with the analyte, thereby creating at least one colored test field 130 for each of the test samples 124.

The calibration method further comprises step d. (method step 138) for acquiring images of the colored test fields 130 by using the camera 116. Specifically, the camera 116 comprised by a smart phone 118 as illustrated in FIG. 1, may be used for acquiring the images of the colored test fields 130. Further, the calibration method comprises step e. (method step 140) for generating color coordinates for the images of the colored test fields 130, by using the color coordinate systems of the set of color coordinate systems, thereby creating a set of color coordinates for the test samples and for the color coordinate systems.

Further, the calibration method comprises step f (method step 142) for providing a set of coding functions. The set of coding functions comprising a plurality of coding functions for transforming color coordinates of a test field 130 into a corresponding concentration of the analyte in the test sample 124. The calibration method further comprises step g. (method step 144) for transforming the set of color coordinates generated in step e. into a set of measured concentrations by using the set of coding functions.

Additionally, the calibration method comprises step h. (method step 146) for comparing the set of measured concentrations with the known concentrations of the test samples 124 and determining a best match color coordinate system and a best match coding function of the set of coding functions for which the set of measured concentrations best matches with the known concentrations. Specifically, the calibration method may particularly be performed such that samples 124 of equidistant concentrations lead to color coordinates in the best match color coordinate system having essentially equidistant color differences.

For example, one, more than one or all of the color coordinates may be taken from different color coordinate systems, specifically from different color coordinate systems from a set of color coordinate systems, and may be used to span the best match color coordinate system. Specifically, the best match color coordinate system may be comprised of more than one, preferably more than two color coordinates. Specifically, a multitude of color coordinates may be referred to as a multi-dimensional parameter. Exemplarily, in order to determine a best match color coordinate system, a discrepancy, e.g., an error, between measured concentrations and known concentrations, e.g., between a measured result and a reference result, may specifically be minimized. Particularly, the error may for example be minimized by adapting a value of parameters, e.g., coefficients, of the color coordinate system, e.g., of the color space. Further, the set of coding functions may specifically comprise more than one coding-function, particularly referred to as multi-dimensional code function. As an example, the multi-dimensional code function may be used to calculate the result, e.g., to determine the analyte concentration of the sample 131.

In FIG. 3, a further embodiment of the calibration method is shown, which, in most parts, corresponds to the method of FIG. 2. Thus, for most steps, reference may be made to the description of FIG. 2 above. As illustrated in FIG. 3, in this embodiment of the calibration method, step e. (method step 140) may comprise three substeps. Specifically, the first substep e1. (method step 148) for generating camera-dependent color coordinates for the images of the colored test field 130, the second substep e2. (method step 150) for transforming the camera-dependent color coordinates into camera-independent color coordinates, by using a first transformation algorithm, and a third substep e3. (method step 152) for transforming the camera-independent color coordinates into color coordinates for the color coordinate systems of the set of color coordinate systems by using a second transformation algorithm, thereby creating the set of color coordinates for the test samples and for the color coordinate systems.

FIG. 4 illustrates a flow chart of an embodiment of a detection method for detecting an analyte in a sample 124. The detection method comprises step A. (method step 154) for providing a camera 116. Specifically, the camera 116 as illustrated in FIG. 1 may be provided. Further, the detection method comprises step B. (method step 156) for calibrating the camera 116 by using the calibration method. Particularly, the calibration method as illustrated in FIG. 2 or 3 may be used for calibrating the camera 116.

Further, the detection method comprises step C. (method step 158) for applying the sample to a test element 128, the test element 128 having at least one test field 130 comprising at least one test chemical configured for performing an optically detectable detection reaction with the analyte, thereby creating at least one colored test field 130 for the sample 124. Specifically, the sample 124 as illustrated separately from the set of test samples 122 in FIG. 1 may be applied to the test element 128, specifically to the test element 128 as illustrated separately from the set of test elements 126 in FIG. 1.

Additionally, the detection method comprises step D. (method step 160) for acquiring at least one image of the at least one colored test field 130. The detection method further comprises step E. (method step 162) for generating color coordinates of the test field 130 by using the best match color coordinate system. In particular, the best match color coordinate system may be comprised of three or four color coordinates from different color coordinate systems of the set of color coordinate systems. Further, the detection method comprises step F. (method step 164) for transforming the color coordinates into a measurement concentration of the analyte in the sample 124 by using the best match coding function.

Figure 5:
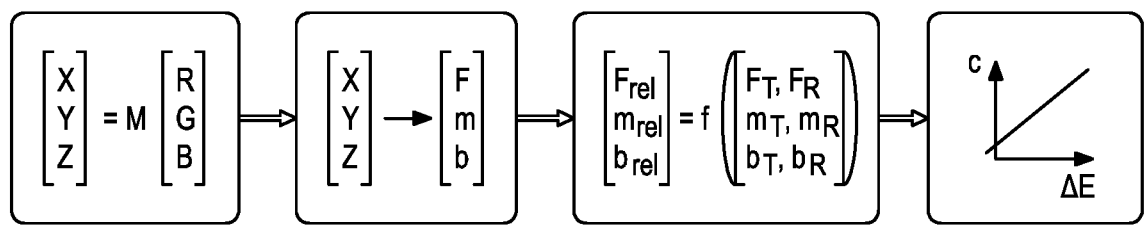
FIG. 5 illustrates part of a flow chart of an embodiment of a calibration method.

FIG. 5 illustrates a part of a flow chart of an embodiment of a calibration method for calibrating a camera 116 for detecting an analyte in a sample 124. This embodiment may be considered as a part of a specific embodiment of the method shown in FIG. 2 or FIG. 3. In particular, a part of the flow chart of the embodiment of the calibration method comprising the substeps e2. and e3. (method steps 150 and 152) and the steps f., g., and h. (method steps 142, 144 and 146) may be illustrated in FIG. 5.

The first transformation algorithm of step e2. (method step 150) may for example contain a matrix operation. Specifically, the first transformation algorithm may contain a matrix operation by using a matrix M, particularly a matrix operation for transforming the camera-dependent color coordinates (R, G, B) into camera-independent color coordinates (X, Y, Z). The first transformation may specifically use the transformation given in Equation (1), particularly, as illustrated in the first box on the left side in FIG. 5.

The second transformation algorithm of step e3. (method step 152) may for example comprise transforming the camera-independent color coordinates into the color coordinates of the set of color coordinates by using parametrized functions. In particular, the camera-independent color coordinates (X, Y, Z) may be transformed into the set of color coordinates (F, m, b) by using the transformations given in Equations 2.1, 2.2 and 2.3. As illustrated in FIG. 5, transforming the camera-independent color coordinates (X, Y, Z) into the set of color coordinates (F, m, b) may be performed subsequently to the performing of the first transformation algorithm. The second transformation algorithm may further take into account the illumination of the test fields specifically by detecting at least one reference color, specifically a reference color of a white field. Particularly, illumination-dependent color coordinates (F, m, b) may be transformed into relative color coordinates ($F_{rel}$, $m_{rel}$, $b_{rel}$) by using one or more of Equations 3.1 to 3.6, as illustrated in the third box from the left in FIG. 5.

Subsequently, steps f g. and h. (method steps 142, 144 and 146) may be performed. Specifically, step h. (method step 146) may be performed such that, over a predetermined measurement range of concentrations, samples 124 of equidistant concentrations lead to color coordinates in the best match color coordinate system having essentially equidistant color differences. As an example, the box on the far right side shown in FIG. 5, illustrates an ideal example, wherein a linear relation exists between an actual analyte concentration (c) of the samples 124 (x-axis) and essentially equidistant color differences (ΔF) of the samples 124 (x-axis).

Figure 6:
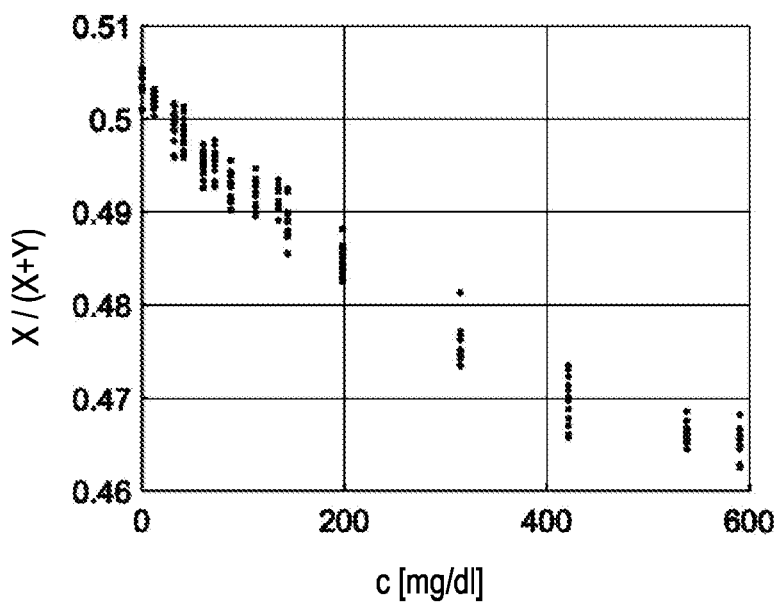
FIG. 6 illustrates a diagram indicating a relationship between actual blood glucose values and a camera-independent color coordinate X.

Further, FIG. 6 illustrates a diagram indicating a relationship between actual blood glucose values (c), for example predefined blood glucose values of the test samples 124, and a ratio X/(X+Y) of camera-independent color coordinates (X,Y,Z). In the shown example, the color coordinate Z is set to Z=0. Specifically, the ratio $a_0 \neq X/(a_1 \cdot X + a_2 \cdot Y)$ of camera-independent color coordinates with parameters $a_0$, $a_1$ and $a_2$ exemplarily set to $a_0=1$, $a_1=1$ and $a_2=1$, is plotted on the y-axis of the diagram illustrated in FIG. 6. Plotted on the x-axis is a concentration of an analyte in the sample 124, such as the actual blood glucose values (c), for example given in milligrams per deciliter (mg/dl). In particular, the diagram shows a non-linear dependency between the ratio of the camera-independent color coordinates and the actual blood glucose values. Thus, in the illustrated example, samples of equidistant concentrations do not lead to essentially equidistant color differences in the chosen color coordinate system (X,Y,Z). Therefore, the chosen color coordinate system may not be a best match color coordinate system and a further performing of the calibration method, as for example illustrated in FIGS. 2 and 3, may be necessary.

Figure 7:
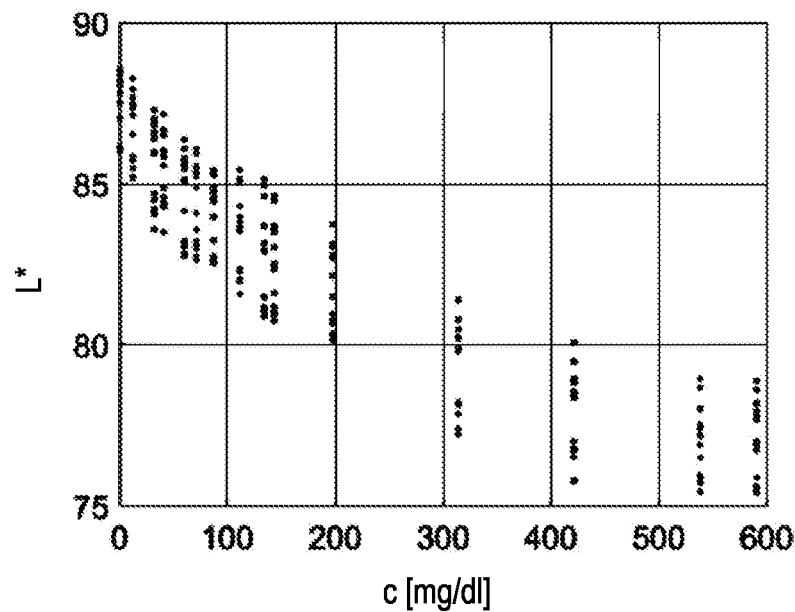
FIGS. 7A to E illustrate embodiments of diagrams indicating a relationship between actual blood glucose values and selected CIE coordinates.
Figure 7:
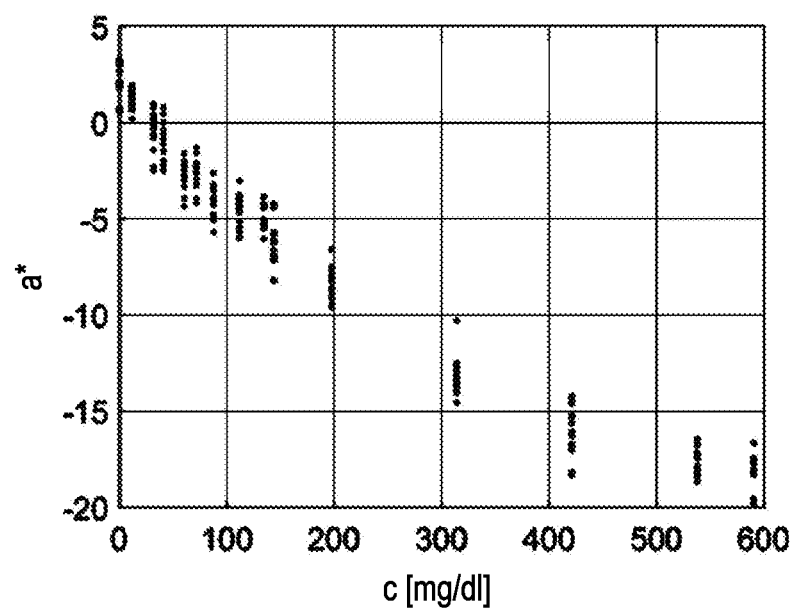
Figure 7:
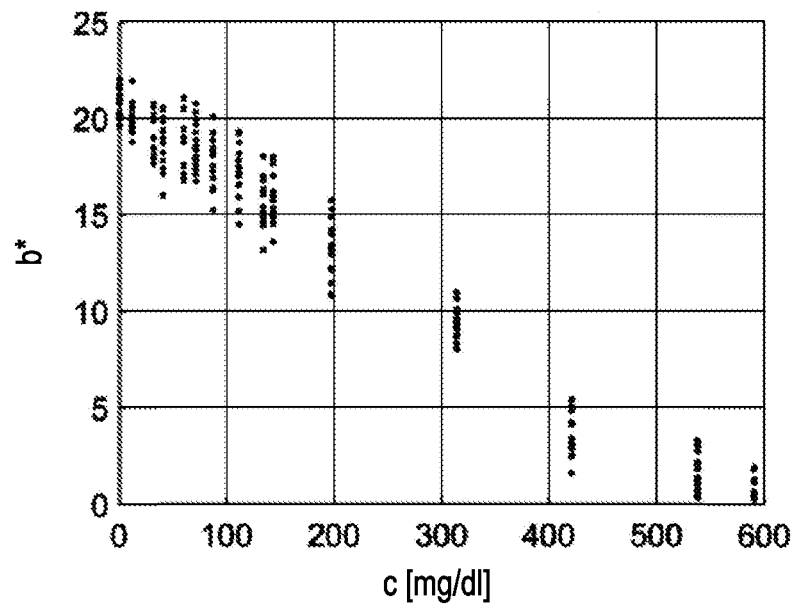
Figure 7:
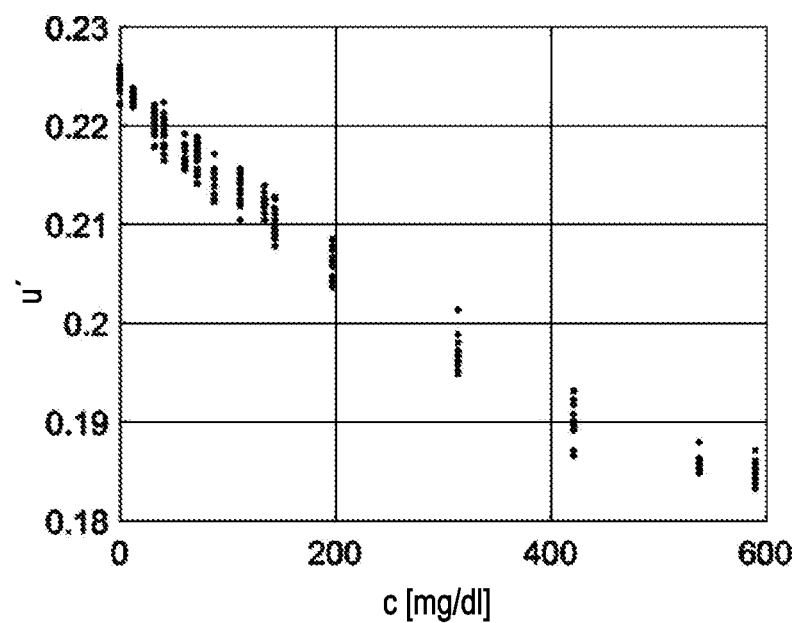
Figure 7:
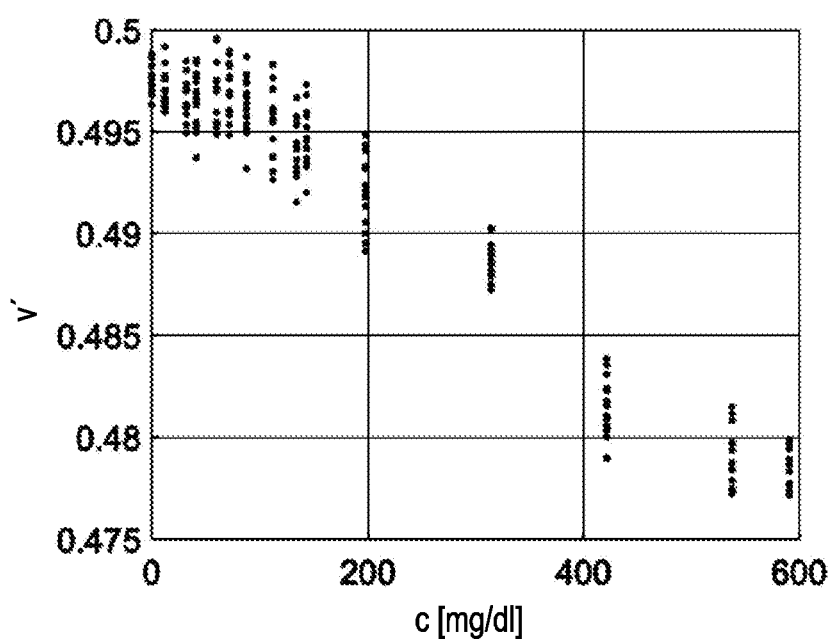

Further, FIGS. 7A to E illustrate embodiments of diagrams indicating a relationship between actual blood glucose values (c) and selected CIE coordinates, such as for example L* in FIG. 7A, a* in FIG. 7B, b* in FIG. 7C, u' in FIG. 7D and v' in FIG. 7E. The diagrams indicate different relationships between the actual blood glucose values and the CIE coordinates for every CIE coordinate. Specifically, as illustrated, different color coordinates have different suitabilities for matching the actual blood glucose concentration, Particularly, the illustrated samples of equidistant concentration are the same for all FIGS. 7A to E, but do not lead to essentially equidistant color differences for all the illustrated CIE coordinates. For example, the diagram illustrated in FIG. 7D indicates a more linear relationship between the color coordinate u' and the samples than the diagram illustrated in FIG. 7B, based on the color coordinate a*.

Figure 8:
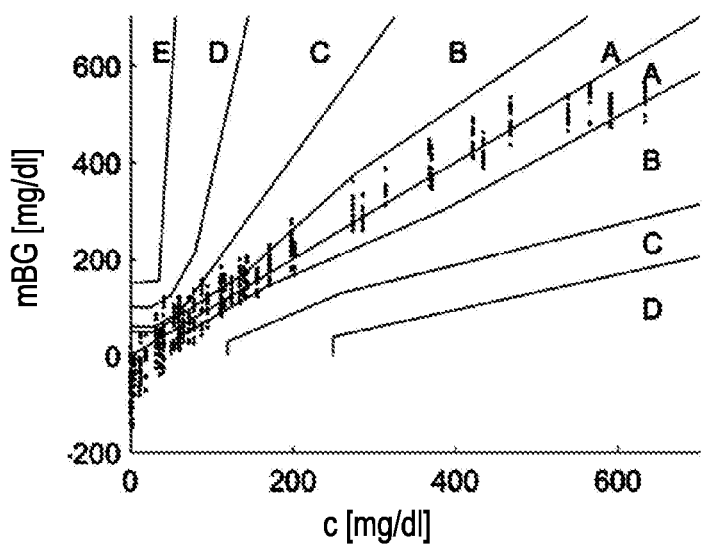
FIGS. 8A and B illustrate embodiments of diagrams indicating a relationship between actual blood glucose values and determined blood glucose values using common methods and systems (Figure A) for the determination of the blood glucose values and using present methods and systems (FIG. 8) according to the present application for the determination of the blood glucose values.
Figure 8:
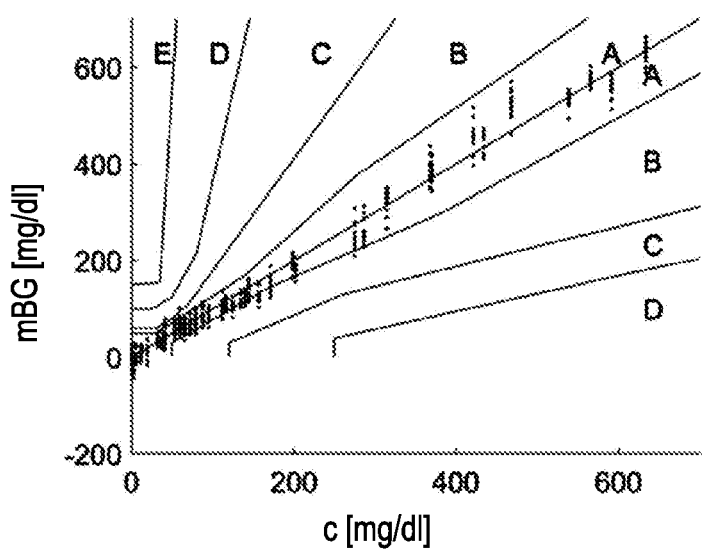

FIG. 8A illustrates an embodiment of a diagram indicating a relationship between actual blood glucose values and determined blood glucose values using common methods and systems for the determination of the blood glucose values. In particular, the diagram illustrated in FIG. 8A indicates the relationship between the actual blood glucose values (c) and determined or measured blood glucose values (mBG) using the CIE color coordinate system L*a*b*.

As opposed thereto, FIG. 8B illustrates an embodiment of a diagram indicating a relationship between actual blood glucose values and determined blood glucose values using present methods and systems according to the present application for the determination of the blood glucose values. Specifically, the diagram illustrated in FIG. 8B indicates the relationship between the actual blood glucose values (c) and determined or measured blood glucose values (mBG) using the best match color coordinate system and the best match coding function. In particular, a comparison of FIGS. 8A and 8B shows an improved accuracy when using the best match color coordinate system and the best match coding function as opposed to using common approaches of determining the blood glucose concentration. Specifically, a lower scattering of determined blood glucose values may be reached when using the best match color coordinate system and the best match coding function. Further, the FIGS. 8A and 8B show regions A to E of an Error-Grid-Analysis, specifically regions A to E of the Parkes Error Grid, quantifying clinical accuracy of a determined blood glucose concentration compared to an actual blood glucose concentration.

Further, the FIGS. 8A and 8B show regions A to E of an Error-Grid-Analysis, specifically regions A to E of the Parkes Error Grid, quantifying clinical accuracy of a determined blood glucose concentration compared to an actual blood glucose concentration. For example blood glucose values within:

Region A contains values within 20% of the reference sensor;
Region B contains values that are outside of 20% but would not lead to inappropriate treatment;
Region C contains values leading to unnecessary treatment;
Region D contains values indicating a potentially dangerous failure to detect hypoglycemia or hyperglycemia, and
Region E contains values that would confuse treatment of hypoglycemia for hyperglycemia and vice versa.

For more information on the Error-Grid-Analysis reference may be made to Clarke W L, Cox D, Gonder-Frederick L A, Carter W, Pohl S L: Evaluating clinical accuracy of systems for self-monitoring of blood glucose. Diabetes Care 10:622-628, 1987.

Both, FIGS. 8A and 8B are based on the same samples, particularly the same set of test samples are used for determining the blood glucose values in both Figures. Table 1 indicates the number of determined blood glucose values for both FIG. 8A and FIG. 8B sorted according to their respective Region.

TABLE 1

Number of determined blood glucose values for both FIG. 8A and FIG. 8B sorted according to their respective Region

| Region | A | B | C | D | E |
|---|---|---|---|---|---|
| number of determined blood glucose values (FIG. 8A) | 521 | 123 | 27 | 1 | 0 |
| number of determined blood glucose values (FIG. 8B) | 613 | 57 | 2 | 0 | 0 |

Specifically, as illustrated in the FIGS. 8A and 8B and as shown by the quantification of the determined blood glucose values given in the table above, the accuracy and the precision of the determined blood glucose values may be improved when using the best match color coordinate system and the best match coding function as opposed to using common approaches of determining the blood glucose concentration.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 system
112 calibration system
114 detection system
116 camera
118 smart phone
119 computer
120 computer network
122 set of test samples
124 test sample
126 set of test elements
128 test element
130 test field
131 sample
132 step a. providing a set of color coordinate systems
134 step b. providing a set of test samples having known concentrations of the analyte
136 step c. applying the test samples to a set of test elements, each test element having at least one test field comprising at least one test chemical configured for performing an optically detectable detection reaction with the analyte, thereby creating at least one colored test field for each of the test samples 138 step d. acquiring images of the colored test fields by using the camera 140 step e. generating color coordinates for the images of the colored test fields, by using the color coordinate systems of the set of color coordinate systems, thereby creating a set of color coordinates for the test samples and for the color coordinate systems 142 step f. providing a set of coding functions, the set of coding functions comprising a plurality of coding functions for transforming color coordinates of a test field into a corresponding concentration of the analyte in the sample 144 step g. transforming the set of color coordinates generated in step e. into a set of measured concentrations by using the set of coding functions 146 step h. comparing the set of measured concentrations with the known concentrations of the test samples and determining a best match color coordinate system and a best match coding function of the set of coding functions for which the set of measured concentrations best matches with the known concentrations 148 step e1. generating camera-dependent color coordinates for the images of the colored test field 150 step e2. transforming the camera-dependent color coordinates into camera-independent color coordinates, by using a first transformation algorithm 152 step e3. transforming the camera-independent color coordinates into color coordinates for the color coordinate systems of the set of color coordinate systems by using a second transformation algorithm, thereby creating the set of color coordinates for the test samples and for the color coordinate systems.

What is claimed is:

1. A calibration method for calibrating a camera for detecting an analyte in a sample, the method comprising:
   a. providing a plurality of different color coordinate systems configured for describing a color of an object;
   b. providing a set of test samples having known concentrations of the analyte;
   c. applying the test samples to a set of test elements, each test element having a test field configured for producing an optically detectable reaction with the analyte, thereby creating a colored test field for each of the test samples;
   d. acquiring images of the colored test fields using the camera;
   e. generating color coordinates for the images of the colored test fields using the color coordinate systems, thereby creating a set of color coordinates for the test samples and for the color coordinate systems;
   f. providing a plurality of coding functions for transforming color coordinates of a test field into a corresponding concentration of the analyte in the sample;
   g. transforming the set of color coordinates generated in step e. into a set of measured concentrations by using the set of coding functions; and
   h. comparing the set of measured concentrations with the known concentrations of the test samples and determining a best match color coordinate system of the plurality of color coordinate systems and a best match coding function of the plurality of coding functions for which the set of measured concentrations best matches the known concentrations.

2. The calibration method according to claim 1, wherein the camera is part of a smart phone.

3. The calibration method according to claim 1, wherein the plurality of color coordinate systems is defined by a set of parametrized functions for transforming color coordinates, wherein a set of parameters of the parametrized functions characterizes each of the color coordinate systems.

4. The calibration method according to claim 1, wherein step e. comprises:
   e1. generating camera-dependent color coordinates for the images of the colored test field;
   e2. transforming the camera-dependent color coordinates into camera-independent color coordinates using a first transformation algorithm; and
   e3. transforming the camera-independent color coordinates into color coordinates for the color coordinate systems using a second transformation algorithm, thereby creating the set of color coordinates for the test samples and for the color coordinate systems.

5. The calibration method according to claim 4, wherein the second transformation algorithm transforms the camera-independent color coordinates into the color coordinates of the set of color coordinates by using parametrized functions.

6. The calibration method according to claim 5, wherein the second transformation algorithm transforms the camera-independent color coordinates (X, Y, Z) into the set of color coordinates (F, m, b) by using the following parametrized functions:

$$F = \begin{cases} P_1 * \sqrt[3]{y_r} - P_2 & \text{if } y_r > \varepsilon \\ \kappa y_r & \text{otherwise} \end{cases} \quad (2.1)$$

$$m = P_3 * F(m' - m'_r) \quad (2.2)$$

$$b = P_3 * F(b' - b'_r) \quad (2.3)$$

with:

$$y_r = \frac{Y}{Y_r}$$

$$m' = \frac{P_4 * X}{P_5 * X + P_6 * Y + P_7 * Z}$$

$$b' = \frac{P_8 * X}{P_9 * X + P_{10} * Y + P_{11} * Z}$$

$$m'_r = \frac{P_4 * X}{P_5 * X + P_6 * Y + P_7 * Z}$$

$$b'_r = \frac{P_8 * X}{P_9 * X + P_{10} * Y + P_{11} * Z}$$

and with $P_1$-$P_{11}$ being parameters.

7. The calibration method according to claim 5, wherein:
   the camera-independent color coordinates are tristimulus values based on the sensitivity of the human eye;
   the second transformation algorithm takes into account the illumination of the test fields;
   illumination-dependent color coordinates (F, m, b) are transformed into relative color coordinates ($F_{rel}$, $m_{rel}$, $b_{rel}$) by using one or more of the following equations:

$$F_{rel} = \frac{F}{F_R} \quad (3.1)$$

$$F_{rel} = \frac{F - F_R}{F_R} \quad (3.2)$$

$$F_{rel} = \frac{F - F_R}{F + F_R} \quad (3.3)$$

$$m_{rel} = \frac{m}{m_R} \quad (3.4)$$

$$m_{rel} = \frac{m - m_R}{m_R} \quad (3.5)$$

$$m_{rel} = \frac{m - m_R}{m + m_R} \quad (3.6)$$

with ($F_R$, $m_R$, $b_R$) being color coordinates derived from an image of an illuminated reference field.

8. The calibration method according to claim 5, wherein the first transformation algorithm is determined in a camera calibration process by acquiring at least one image of at least one reference color field having known camera-independent color coordinates.

9. The calibration method according to claim 1, wherein step h is performed such that, over a predetermined measurement range of concentrations, samples of equidistant concentrations lead to color coordinates in the best match color coordinate system having essentially equidistant color differences.

10. A detection method for detecting an analyte in a sample, the method comprising:
   A. providing a camera;
   B. calibrating the camera using the calibration method according to claim 1;
   C. applying the sample to a test element, the test element having a test field configured for performing an optically detectable detection reaction with the analyte, thereby creating at least one colored test field for the sample;
   D. acquiring an image of the colored test field;
   E. generating color coordinates of the test field by using the best match color coordinate system;
   F. transforming the color coordinates into a measurement concentration of the analyte in the sample by using the best match coding function.

11. A calibration system for calibrating a camera for the purpose of detecting an analyte in a sample using the camera, the calibration system comprising at least one computer or computer network, a set of test samples having known concentrations of the analyte and a set of test elements, each test element having at least one test field, the calibration system being configured for performing the calibration method of claim 1.

12. A detection system for detecting an analyte in a sample by using a test element having a test field configured for performing an optically detectable reaction with the analyte, the detection system comprising a camera, at least one computer or computer network, at least one sample and at least one test element having a test field, the detection system configured for performing the detection method according to claim 1.

13. A non-transitory computer readable medium having stored thereon computer-executable instructions for performing the method according to claim 1.

\* \* \* \* \*